(12) United States Patent
Larsen

(10) Patent No.: US 8,768,720 B2
(45) Date of Patent: Jul. 1, 2014

(54) LOCATION LIMITED CHECK-IN KIOSK METHOD AND APPARATUS

(75) Inventor: Steven J. Larsen, Cross Plains, WI (US)

(73) Assignee: Epic Systems Corporation, Verona, WI (US)

( * ) Notice: Subject to any disclaimer, the term of this patent is extended or adjusted under 35 U.S.C. 154(b) by 1936 days.

(21) Appl. No.: 11/786,572

(22) Filed: Apr. 12, 2007

(65) Prior Publication Data

US 2008/0255876 A1  Oct. 16, 2008

(51) Int. Cl.
*G06Q 10/00* (2012.01)
*G06Q 50/00* (2012.01)

(52) U.S. Cl.
USPC ................................... 705/2; 705/3

(58) Field of Classification Search
USPC .......................................... 705/2–3
See application file for complete search history.

(56) References Cited

U.S. PATENT DOCUMENTS

| | | |
|---|---|---|
| 5,726,688 A | 3/1998 | Siefert et al. |
| 6,094,640 A | 7/2000 | Goheen |
| 6,121,968 A | 9/2000 | Arcuri et al. |
| 6,232,972 B1 | 5/2001 | Arcuri et al. |
| 6,640,212 B1 | 10/2003 | Rosse |
| 6,847,387 B2 | 1/2005 | Roth |
| 6,981,242 B2 | 12/2005 | Lehmeier et al. |
| 2002/0046278 A1* | 4/2002 | Hays et al. ..................... 709/225 |
| 2002/0116235 A1 | 8/2002 | Grimm et al. |
| 2003/0033079 A1 | 2/2003 | Endicott |
| 2004/0138924 A1 | 7/2004 | Pristine |
| 2004/0186744 A1 | 9/2004 | Lux |
| 2004/0260577 A1* | 12/2004 | Dahlin et al. ..................... 705/2 |
| 2005/0010485 A1 | 1/2005 | Sarvestani et al. |
| 2005/0044508 A1 | 2/2005 | Stockton |
| 2005/0078643 A1* | 4/2005 | Archiable ..................... 370/338 |

(Continued)

FOREIGN PATENT DOCUMENTS

| | | |
|---|---|---|
| EP | 0 891 066 A2 | 9/1998 |
| GB | 2 228 123 | 8/1990 |

(Continued)

OTHER PUBLICATIONS

Cho, John M., "Using Kiosks for Patient Self-Service Check-in as a Technology Portal to Health Forces throughout a Health Care Network", Dewitt Army Community Hospital Fort Belvoir VA, Sep. 2004.*

(Continued)

*Primary Examiner* — Justin M Pats
*Assistant Examiner* — Amber A Misiaszek
(74) *Attorney, Agent, or Firm* — Quarles & Brady LLP

(57) ABSTRACT

A method and system for helping a client check in for a scheduled activity wherein at least first and second subsets of activities occur proximate first and second locations, respectively, the method comprising the steps of providing a check in resource at the second location for checking clients in for the second subset of activities, associating at least a first electronic kiosk with the first subset activities, positioning the first kiosk at the first location for use by clients to check in for first subset activities, via the first kiosk, receiving identifying information from a first client, identifying at least a first currently scheduled activity for the first client, determining that the first currently scheduled activity is one of the second subset activities and via the first kiosk, indicating that the first client cannot check in for the first currently scheduled activity via the first kiosk.

35 Claims, 14 Drawing Sheets

(56) References Cited

U.S. PATENT DOCUMENTS

| | | | |
|---|---|---|---|
| 2005/0125265 A1 | 6/2005 | Bramnick et al. | |
| 2005/0131856 A1 | 6/2005 | O'Dea | |
| 2005/0144642 A1 | 6/2005 | Ratterman | |
| 2005/0234741 A1 | 10/2005 | Rana et al. | |
| 2005/0261942 A1* | 11/2005 | Wheeler | 705/3 |
| 2006/0000903 A1 | 1/2006 | Barry et al. | |
| 2006/0111941 A1* | 5/2006 | Blom | 705/2 |
| 2006/0206818 A1 | 9/2006 | Utter et al. | |
| 2006/0261942 A1 | 11/2006 | Frank | |
| 2006/0277071 A1 | 12/2006 | Shufeldt | |
| 2007/0050197 A1 | 3/2007 | Efron et al. | |

FOREIGN PATENT DOCUMENTS

| | | |
|---|---|---|
| WO | WO 97/17680 | 5/1997 |
| WO | WO 98/40826 | 9/1998 |
| WO | WO 2005/010636 A2 | 3/2005 |

OTHER PUBLICATIONS

Touch Vision; Check In; www.touchvision.com webpage.
Galvanon; Case Study—MediKiosk; 2002-2005 Galvanon, Inc.
WEBPAGE, Welcome to Innovation Health Centers; www.otechgroupllc.com.
St. Claire Interactive International; St. Clair Interactive Communications, Inc. Kiosk Administrator brochure, Toronto Ontario Canada.
NEC Solutions America; PersonalPass—Automated Patient ID & Admissions Facility Mapping; www.necsam.com/healthcare; 2005.
PAERS, LTD; Patient Access Electronic Record System; 2004 PAERS, Ltd.

* cited by examiner

| Way Finder Database | | | | |
|---|---|---|---|---|
| Current Kiosk | Destination Kiosk | Map | Directions | Estimated Time Of Travel (ETOT) |
| 26a1 | 26b | M (26a1-26b) | D (26a1-26b) | 7 minutes |
| 26a1 | 26c | M (26a1-26c) | D (26a1-26c) | 16 minutes |
| . . . | | | | |
| 26a1 | 26z | M (26a1-26z) | D (26a1-26z) | 28 minutes |
| 26a2 | 26b | M (26a2-26b) | D (26a2-26b) | 7 minutes |
| . . . | | | | |
| 26b | 26a1 | M (26b-26a1) | D (26b-2561) | 7 minutes |
| . . . | | | | |
| 26c | 26a1 | M (26c-26a1) | D (26c-26a1) | 12 minutes |
| . . . | | | | |
| 26z | 26a1 | M (26z-26a1) | D (26z-26a1) | 28 minutes |
| . . . | | | | |

Fig. 4

LOCATION LIMITED CHECK-IN KIOSK METHOD AND APPARATUS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to automated check in kiosks for use by clients to access health care related self-service options and more specifically to a system of kiosks where distinct subsets of self-service options are to be provided at different kiosks and where each system kiosk is aware of which options are to be provided at different kiosks and is capable of providing guidance for patients that attempt to perform an activity at incorrect kiosks.

In the health care industry profits are extremely important. As in most industries, one generally effective way to increase profits has been through growth such that many health care service providers have become, in effect, one stop shops for virtually all medical needs of patients. Thus, large service providers may have several hundreds or even thousands of physicians that specialize in different medical services and that work in many different medical facilities despite their common affiliation. In fact, some service providers are so large that they have complete campuses or even several separate campuses that each includes many buildings that house different health care specialty departments or clinics. Herein the term "enterprise" will be used to refer to service providers that have either geographically dispersed facilities or campuses (e.g., multiple campuses located at different locations about a metropolitan area), or multiple departments/clinics located in the same physical location. In some cases multiple departments or clinics are located in a large single building or in attached buildings.

Where departments are spaced apart within a facility or throughout a campus or at separate campuses, separate patient check in resources are typically located proximate each of the departments so that patients can check in for appointments proximate the locations at which their appointments are to occur. Historically medical facility check in resources have included receptionists that use check in terminals to register patients prior to appointments. Where a check in receptionist is provided, when a first patient arrives at a department to attend a previously scheduled appointment and a receptionist is not attending to another patient, the receptionist greets the first patient, obtains patient identifying information from the patient, confirms that the patient has an appointment at the department, may confirm or update insurance information, checks the patient in for the appointment and typically directs the patient to a waiting area associated with and proximate the department until a physician and/or other resources (e.g., equipment, examination or procedure rooms, etc.) required for the patient's appointment are available. In some cases patients may wait in a waiting area for an extended period (e.g., 30-45 minutes) prior to commencement of their appointment either because the patient arrived for the appointment well in advance of the time slot reserved for the appointment or because the physician and/or other resources required for their appointment are occupied longer than anticipated.

Another effective way to increase profits has been to use technology to increase efficiency and productivity whenever possible. Recently, as in other industries such as the air travel or hotel industries, technology has been applied to the check in process. To this end, check in kiosks have been developed that allow patients to self-check in for appointments, thereby alleviating or substantially reducing the need for receptionists at each department within a large facility. In some cases it has been contemplated that check in kiosks may be placed proximate a main entry into a medical facility or campus where, at the end of a check in process, the kiosk provides directions to a physician's office, department, or other location where a patient's appointment is to occur. In other cases it has been contemplated that patient check in kiosks may be placed at various locations throughout a provider facility or campus. The placement and distribution of kiosks within or across an organization is a matter of implementation, and the invention contemplates countless variations; the primary requirement is that the locations exist and a record of relative location to each other and to the services provided exists.

When a patient arrives at a check in kiosk to check in, the patient provides patient identifying information via the kiosk. After the patient is identified, patient appointments are presented to the patient, the patient selects appointments to check in for and is then checked in for the appointments. At the end of the check in process the kiosk instructs the patient to wait in a waiting area until called for the appointment.

While check in kiosks have reduced the need for receptionist services, in some cases patient check in kiosks can result in patient confusion and missed or delayed appointments. For instance, where kiosks are placed at main facility or campus entries, a patient may check in and then, despite receiving directions to an appointment location via the kiosk, may lose his way or be delayed along his way to an appointment location and thus may be late for the appointment. Patient confusion and delay is particularly likely in the case of large facilities and/or campuses where there may be long and circuitous travel paths between entry points and appointment locations.

As another instance, in any case where each kiosk in a facility or on a campus can be used to check in appointments for multiple departments, a patient may end up waiting for an appointment in a wrong waiting area (i.e., a waiting area that is remote from a location at which the appointment is to take place). Where a patient checks in using a kiosk that is remote from the department where the patient's appointment is to take place, even in cases where directions are presented to the patient that instruct the patient to travel to a different part of a facility/campus to attend the appointment, the patient may assume that the patient is to wait in the waiting area proximate the kiosk used to check in and hence may wait in the wrong waiting area and completely miss his appointment. In this regard, in the past, where receptionists have been stationed proximate each department in a large facility to check patients in, it was normal to wait in the waiting area adjacent the check in location (i.e., adjacent the check in receptionist) and therefore, it would be natural for a patient to assume that the patient should wait in the waiting area adjacent to a kiosk used to check in. In addition, while waiting for their appointment in the wrong waiting area, the patient may naturally assume that any delay in being called for his appointment is attributable to routine resource overbooking and therefore may not question a delay until after the patient's appointment time has come and gone. Missed and delayed appointments frustrate patients and service providers and waste valuable health care resources.

BRIEF SUMMARY OF THE INVENTION

It has been recognized that the patient confusion and missed or delayed appointments that can result from use of check in kiosks can be avoided by limiting kiosk capabilities as a function of kiosk location, and further by making kiosks aware of their location relative to each other and to the locations where specific services are provided in the facility. To this end, according to one aspect of the present invention, in cases where kiosks are located at many different locations within a facility or on a campus and where each kiosk is proximate one or a small number of departments, it is contemplated that each kiosk may be programmed such that the kiosk can only be used to check in patients for appointments at proximate departments. Here, where a patient attempts to check in using a kiosk that is remote from his appointment, a warning is provided that the kiosk cannot be used to check in for the appointment and, in at least some cases, instructions are provided that identify a facility and/or campus location at which the patient may check in for his appointment. In some cases directions are provided to a patient to guide the patient to a kiosk for check in.

It has also been recognized that in some cases a kiosk and related system components may be programmed to, when a patient that attempts to check in for an appointment at a location remote from the location at which the appointment is to take place, provide notice to a receptionist or the like that the patient is in a facility or on a campus and that the patient is likely in transit to the appointment location. Here, the kiosk and related system components may also be programmed to account for the likely travel time from the kiosk used to attempt to check in to the appointment location and may provide notice to one or both of the patient and the receptionist regarding likelihood that the patient will be late for the appointment.

In some cases where estimated travel time from a kiosk to a location at which an appointment is to take place will likely cause the patient to miss his appointment, notice may be provided to one or both of the patient and the receptionist. In cases where estimated travel time will definitely cause the patient to miss the appointment, notice can be provided to one or both of the patient and receptionist. Where a patient will miss his appointment the kiosk may be programmed to present the patient with an option to reschedule the appointment for the same day or for a subsequent day. Here, long estimated travel times may occur in the case of large facilities and/or campuses or in cases where a patient is completely at a wrong facility or campus (i.e., where a patient may have to drive to another geographic location associated with a health care service provider).

According to at least one embodiment the invention includes a method for helping a client check in for a scheduled activity wherein at least first and second subsets of activities occur proximate first and second locations, respectively, the method comprising the steps of providing a check in resource at the second location for checking clients in for the second subset of activities, associating at least a first electronic kiosk with the first subset activities, positioning the first kiosk at the first location for use by clients to check in for first subset activities, via the first kiosk, receiving identifying information from a first client, identifying at least a first currently scheduled activity for the first client, determining that the first currently scheduled activity is one of the second subset activities and, via the first kiosk, indicating that the first client cannot check in for the first currently scheduled activity via the first kiosk.

In at least some embodiments the method further includes the step of, after determining that the first currently scheduled activity is one of the second subset activities, indicating that the first client must check in for the first currently scheduled activity at the second location. In some cases the method further includes the steps of identifying an estimated travel time for the first client to travel from the first location to the second location and presenting the estimated travel time to the first client via the kiosk. In some cases the method further includes the step of, after determining that the first currently scheduled activity is one of the second subset activities, providing notice to a receptionist indicating that the first client is at the first location.

In some embodiments the first activity is scheduled to commence at a first time, the method further including the steps of using the current time and the estimated travel time to identify a predicted arrival time of the first client at the second location and, when the predicted arrival time is subsequent to the first time, providing notice to a receptionist. In some embodiments the first activity is scheduled to commence at a first time, the method further including the steps of using the current time and the estimated travel time to identify a predicted arrival time of the first client at the second location and, when the predicted arrival time is subsequent to the first time, providing notice to the first client via the first kiosk.

In some embodiments the at least a first resource is required to perform the first activity, the method further including the steps of, when the predicted arrival time is substantially subsequent to the first time, indicating that the client should reschedule the first activity for a time subsequent to the first time. In some embodiments the at least a first resource is required to perform the first activity, the method further including the steps of, when the predicted arrival time is substantially subsequent to the first time, accessing a resource schedule for the first resource and attempting to identify an open schedule time slot subsequent to the first time for performing the first activity for the first client.

In at least some embodiments the method further includes the steps of, when at least one open schedule time slot is identified, presenting the time slot to the first client via the kiosk and facilitating rescheduling of the first activity. In some embodiments the method further includes the step of providing instructions via the kiosk directing the client from the first location to the second location. In some cases the step of providing instructions includes providing a graphical map via the kiosk. In some cases the kiosk includes a printer and wherein the step of providing a graphical map includes printing out a hard copy of the graphical map. In some cases the first and second locations are in a single facility. In some cases the step of providing check in resources at the second location includes providing a second electronic kiosk at the second location for checking clients in for second subset activities.

In some embodiments the method further includes the steps of, via the second kiosk, receiving identifying information from a second client, identifying at least a first currently scheduled activity for the second client, determining that the first currently scheduled activity for the second client is one of the first subset activities and, via the second kiosk, indicating that the second client must check in for the first currently scheduled activity for the second client at the first location.

In some cases the at least a third subset of activities occur proximate a third location, the method further including the steps of providing at least a third electronic kiosk at the third location for checking clients in for third subset activities, when the first currently scheduled activity is one of the third subset activities, indicating via the first kiosk that the first client must check in for the first currently scheduled activity at the third location and, when the first currently scheduled activity for the second client is one of the third subset activities, indicating via the second kiosk that the second client must check in for the first currently scheduled activity for the second client at the third location. In some cases the method further includes the steps of, via the first kiosk, identifying at least a second currently scheduled activity for the first client, determining that the second currently scheduled activity for the first client is one of the first subset activities and via the first kiosk, enabling the first client to check in for the second currently scheduled activity via the first kiosk. In some cases the clients are patients and wherein the kiosks are associated with a medical facility.

According to some embodiments the invention includes a method for helping a client check in for a scheduled activity wherein at least first and second subsets of activities occur proximate first and second locations, respectively, wherein clients use wireless communication devices (WCDs) to communicate with a wireless communication system, the method comprising the steps of providing a wireless location determining system, receiving identifying information from a first client via a first WCD used by the first client, identifying at least a first currently scheduled activity for the first client, determining that the first currently scheduled activity is one of the second subset activities, identifying the location of the first WCD, when the first WCD is located at the first location, indicating via the first WCD that the client must be at the second location to check in for the first currently scheduled activity.

In some cases the method further includes the steps of receiving identifying information from a second client via a second WCD used by the second client, identifying at least a first currently scheduled activity for the second client, determining that the first currently scheduled activity for the second client is one of the first subset activities, identifying the location of the second WCD, when the second WCD is located at the second location, indicating via the second WCD that the second client must be at the first location to check in for the first currently scheduled activity for the second client.

According to still other embodiments the invention may include a method for helping a client check in for a scheduled activity wherein first through Nth subsets of activities occur proximate first through Nth locations, respectively, the method comprising the steps of, providing a check in resource at the second location for checking clients in for the second subset of activities, associating first through Nth electronic kiosks with the first through Nth subsets of activities, respectively, positioning the first through Nth kiosks at the first through Nth locations for use by clients to check in for first through Nth subsets of activities, respectively, via at least the first kiosks: receiving identifying information from a first client, identifying at least a first currently scheduled activity for the first client, determining that the first currently scheduled activity is one of an Xth subset activities associated with an Xth kiosk and that occur proximate an Xth location where X is between 2 and N and indicating that the first client must check in for the first currently scheduled activity at the Xth location.

In some cases the method further includes the steps of identifying an estimated travel time for the first client to travel from the first location to the Xth location and presenting the estimated travel time to the first client via the first kiosk. Ion some embodiments the first activity is scheduled to commence at a first time, the method further including the steps of using the current time and the estimated travel time to identify a predicted arrival time of the first client at the Xth location and, when the predicted arrival time is subsequent to the first time, providing notice to the first client via the first kiosk. Some cases further include the step of providing instructions via the kiosk directing the client from the first location to the second location. Still other embodiments further include the steps of, via the first kiosk: identifying at least a second currently scheduled activity for the first client, determining that the second currently scheduled activity for the first client is one of the first subset activities and enabling the first client to check in for the second currently scheduled activity via the first kiosk.

Some embodiments include a system for helping a client check in for a scheduled activity wherein at least first and second subsets of activities occur proximate first and second locations, respectively, the system comprising a database storing currently scheduled appointments for clients, a processor, a check in resource located at the second location for checking clients in for the second subset of activities, a first interface device associated with the first subset activities and located at the first location for receiving client identifying information and providing information to clients and also for use by clients to check in for first subset activities, a processor programmed to, when client identifying information is provided via the first interface device, identify the client as a first client, identify at least a first currently scheduled activity for the first client, determine that the first currently scheduled activity is one of the second subset activities and, via the first interface device, indicate that the first client cannot check in for the first currently scheduled activity via the first interface device.

In some cases the processor is further programmed to, after determining that the first currently scheduled activity is one of the second subset activities, indicate that the first client must check in for the first currently scheduled activity at the second location. In some cases the processor is further programmed to identify an estimated travel time for the first client to travel from the first location to the second location and present the estimated travel time to the first client via the first interface device. In some cases the first activity is scheduled to commence at a first time, the processor further programmed to use the current time and the estimated travel time to identify a predicted arrival time of the first client at the second location and, when the predicted arrival time is subsequent to the first time, provide notice to the first client via the first interface device.

In some cases the at least a first resource is required to perform the first activity, the processor further programmed to, when the predicted arrival time is substantially subsequent to the first time, indicate that the first client should reschedule the first activity for a time subsequent to the first time via the first interface device. In some cases the processor is further programmed to provide instructions via the first interface device directing the first client from the first location to the second location. In some cases the first and second locations are in different buildings. In some cases the check in resource at the second location includes a second interface device at the second location for checking clients in for second subset activities and wherein the second interface device can be used to input client identifying information.

In some embodiments the processor is further programmed to, when client identifying information is provided via the second interface device identify the client as a second client, identify at least a first currently scheduled activity for the second client, determine that the first currently scheduled activity for the second client is one of the first subset activities and via the second interface device, indicate that the second client must check in for the first currently scheduled activity for the second client via the first interface device.

In some cases the processor is further programmed to perform the steps of identifying at least a second currently scheduled activity for the first client, determining that the second currently scheduled activity for the first client is one of the first subset activities and, via the first interface device, enabling the first client to check in for the second currently scheduled activity using the first interface device. In some cases the clients are patients and wherein the interface devices are associated with a medical facility.

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention can be employed. Other aspects, advantages and novel features of the invention will become apparent from the following detailed description of the invention when considered in conjunction with the drawings.

BRIEF DESCRIPTION OF THE SEVERAL VIEWS OF THE DRAWINGS

FIG. 4 is an exemplary way finder database that may be used by the system of FIG. 1;

FIG. 5 is a flow chart illustrating a method whereby one of the kiosks in FIG. 1 is used to facilitate a patient check in process where the kiosk limits the appointments that can be checked-in thereby by as function of the location of the kiosk and the locations of the appointments to be checked in;

DETAILED DESCRIPTION OF THE INVENTION

Figure 1:
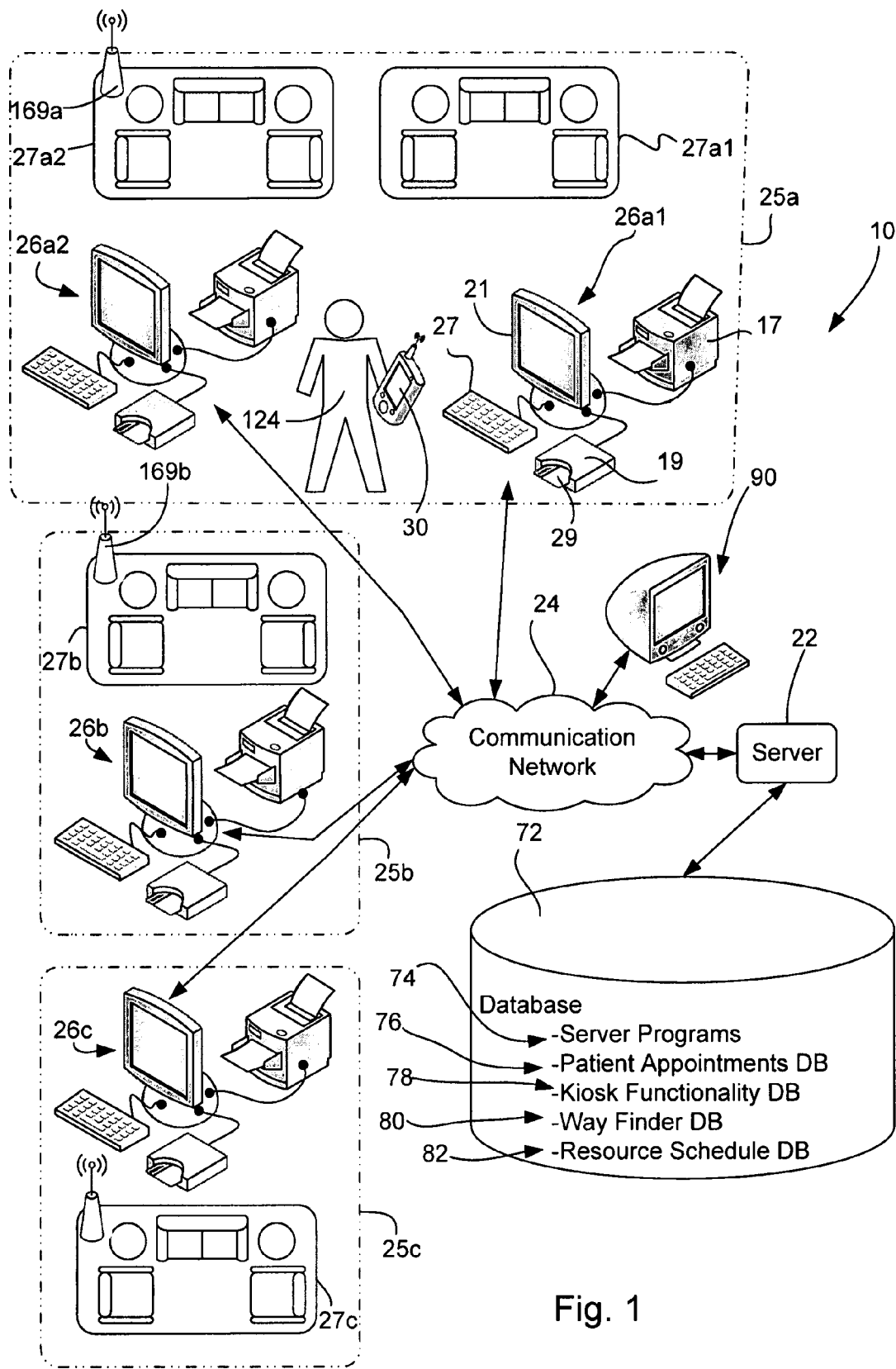
FIG. 1 is a schematic diagram illustrating an exemplary check in system for a medical facility according to at least some aspects of the invention.

Referring now to the drawings wherein like reference numerals correspond to similar elements throughout the several view and, more specifically, referring to FIG. 1, the present invention will be described in the context of an exemplary health care facility information system 10 that includes, among other components, a server/processor 22, a database 72, a plurality of patient accessible and useable kiosks or interface devices 26a1, 26a2, 26b, 26c, etc., at least one receptionist/administrator terminal 90 and a communication network 24. Server 22 runs software programs that perform various methods and processes that are contemplated by the present invention, to provide browser-type screen shots to the kiosks 26a1, 26a2, 26b, etc., and to receive input from the kiosks. Each of kiosks 26a1, 26a2, 26b, etc., may take any of several forms including workstations, personal computers, lap tops, thin client-type devices, etc. Where the kiosks are more than thin clients, in at least some embodiments, each kiosk may perform all or at least a subset of the steps required to perform the inventive processes. When the kiosks are thin client-type devices, each kiosk operates primarily as a human-server interface device for input/output between a patient and server 22 where server 22 performs most or all of the inventive process steps. Hereinafter, unless indicated otherwise and the interest of simplifying this explanation, it will be assumed that each kiosk 26a1, 26a2, 26b, etc., is a thin client-type device.

Each of the kiosks 26a1, 26a2, 26b, etc., is similarly constructed and operates in a similar fashion and therefore, in the interest of simplifying this explanation, only kiosk 26a1 will be described here in any detail. Kiosk 26a1 includes a flat panel display 21, an input device 27, a card reader 19 and printer 17. Input device 27 is shown as a keyboard but may include other input devices such as a mouse device, a trackball-type device, etc., and, is generally provided for, as the label implies, entering information into system 10 for use by server 22. In the present case, it will be assumed that input device(s) 27 includes a keyboard for entering text-type information and a mouse-type device (not illustrated) for moving a mouse-controlled cursor (see 214 in FIG. 7) around on display 21.

Card reader 19 includes a slot for receiving identification cards from patients for identification purposes. In this regard, card 29 may be a credit card, a drivers license, a dedicated insurance card, a health care card, etc., from which, when slipped into the reader 19, information can be read to uniquely identify a patient using the card. To this end, prior to using one of the kiosks to check in for an appointment, it is contemplated that patient identities will be associated with patient unique cards in database 72.

Receptionist/administrator terminal 90 may take any of several forms including a workstation, a personal computer, a thin client, etc. and, in general, includes a display and one or more types of input devices (not labeled, e.g., a keyboard, a mouse controlled cursor). As the label implies, terminal 90 is used by a receptionist in some applications and by a system administrator in other applications.

Referring still to FIG. 1, network 24 is a communication network and may include one or all of local area networks (LANs), wide area networks (WANs), the Internet, etc. Network 24 may include hardwired components and/or components that communicate wirelessly using Bluetooth and/or 802.11b or other communication protocols. Network 24 links kiosks 26a1, 26a2, 26b, etc., and terminal 90 to server 22.

Database 72 is linked to server 22 and stores programs 74 performed by server 22 and various sub-databases (also referred to as "databases" hereinafter) that may be used by the server software to perform inventive methods. To this end, exemplary sub-databases include a patient appointments database 76 and a kiosk functionality database 78. In addition, in at least some inventive embodiment, database 72 will include a way finder database 80 and/or a resource schedule database 82 which are described in greater detail below.

Here, while each of the databases 74, 76, 78, 80 and 82 is described as a separate database, it should be appreciated that, in at least some embodiments, all or subsets of the described databases may be combined into one or a smaller group of databases. In addition, it should be appreciated, that while all of the databases described herein are described as being part of database 72, each of the databases may be stored completely separately from the other databases.

Referring once again to FIG. 1, in the present description, in the interest of simplifying this explanation, it will be assumed that system 10 is used within a single large building facility that includes different departments spread out throughout the facility. It will also be assumed that a separate waiting area is provided for each facility department. In FIG. 1, exemplary department waiting areas are identified by labels 27a1, 27a2, 27b, 27c, etc. Hereafter, labels 27a1, 27a2, 27b, 27c, etc., will be used to refer to distinct facility departments. Moreover, it will be assumed that each of the departments will be associated with a specific location or zone within the facility where exemplary locations in FIG. 1 are labeled 25a, 25b, 25c, etc. Thus, in FIG. 1, exemplary departments 27a1 and 27a2 are both associated with location 25a. Similarly, department 27b is associated with location 25b and department 27c is associated with location 25c.

While the system and example described herein is described in the context of a large facility with multiple departments, it should be appreciated that system 10 may be employed in other larger environments including, but not limited to, large health care service provider campuses that include multiple related buildings and larger enterprises where, for instance, an exemplary enterprise may include a plurality of geographically spaced apart campuses or building facilities (e.g., campuses at spaced apart locations in a metropolitan area, within a state, etc.).

Figure 2:
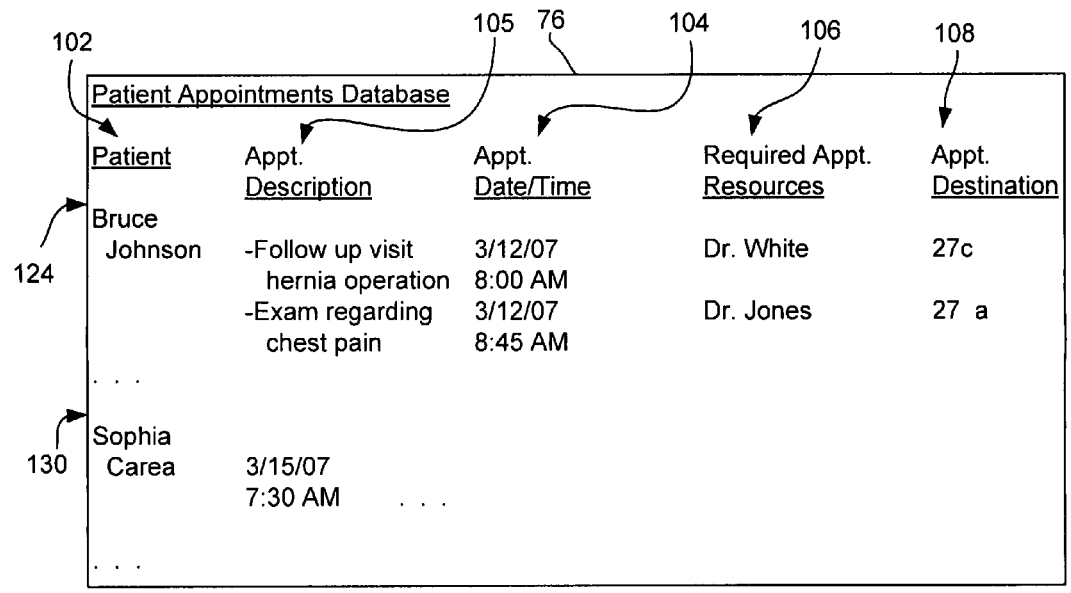
FIG. 2 is an exemplary patient appointments database that may be used by the system of FIG. 1.
Figure 3:
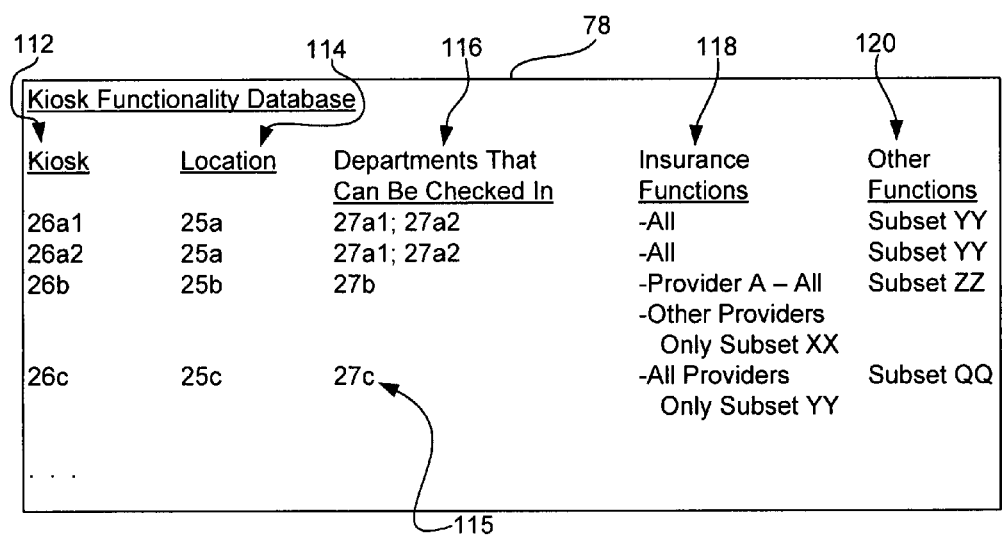
FIG. 3 is an exemplary kiosk functionality database that may be used by the system of FIG. 1.

Referring still to FIG. 1 and now also to FIG. 2, an exemplary patient appointments or activities database 76 is shown in FIG. 2 that includes several different types of information that are presented in a table format. Here, while information in database 76 and other databases described with respect to FIGS. 3 and 4 are shown in table format, it should be appreciated that each one of the databases may take any of several different forms. Here, the important aspect of each of the databases is the substance of the database and not the format thereof.

In FIG. 2, patient appointments database 76 includes a patient column 102, an appointment description column 105, an appointment date/time column 104, a required appointment resources column 106 and an appointment department column 108. Patient column 102 as the label implies, lists all facility patients that currently have scheduled appointments at the facility. Exemplary patients in column 102 include Bruce Johnson 104 and Sophia Carea 103.

Appointment description column 105 lists a subset of appointments for each one of the patients in column 102. To this end, exemplary appointments for Bruce Johnson include a follow up visit related to a hernia operation and an examination regarding chest pain. Appointment date/time column 104 lists the date and time of each one of the appointments in column 104. Each of the appointments for Bruce Johnson is scheduled for Mar. 12, 2007 where the hernia operation follow up is to occur at 8:00 a.m. and the chest pain examination is to occur at 8:45 a.m.

Required appointment resources column 106 lists each one of the facility resources or multiple resources that are required for each one of the appointments in column 105. Exemplary resources in column 106 include Dr. White who is required for the hernia operation follow up and Dr. Jones who is required for the chest pain examination. Other resources may include equipment, exam rooms, employee specialists, etc., that are required for an appointment. Appointment department column 108 lists separate facility department for each one of the appointments in column 105. In this regard, column 108 lists departments 27c and 27a (see again FIG. 1) for the hernia operation follow up and chest pain exam, respectively.

Referring now to FIG. 1 and also to FIG. 3, an exemplary kiosk functionality database 78 is shown in FIG. 3 that includes a kiosk column 112, a location column 114, a departments that can be checked in column 116, an insurance function column 118 and an other functions column 112. Kiosk column 112 lists each facility kiosk. Exemplary kiosks in column 112 include kiosks 26a1, 26a2, 26b, 236c, etc. Location column 114 indicates the location of each one of the kiosks in column 112. Thus, location column 114 indicates that kiosk 26a1 is at location 25a which is consistent with FIG. 1. Similarly, column 114 indicates that kiosk 26b is at location 25b and that kiosk 26c is at location 25c.

Departments that can be checked in column 116, as the label implies, indicates departments for which appointments can be checked in using one of the kiosks in column 112. As shown in FIG. 3, kiosk 26a1 can be used to check in patients for appointments in departments 27a1 and 27a2. Similarly, kiosk 26b and kiosk 26c can be used to check patients for appointments in departments 27b and 27c, respectively. Insurance and other functions columns 118 and 120 are described below.

Referring once again to FIG. 1 and now also to FIG. 4, exemplary way finder database 80 in FIG. 4 includes information that can be presented to a patient to help the patient travel to a facility location at which the patient appointment is to occur. Database 80 includes a current kiosk column 142, a destination kiosk column 144, a map column 146, a directions column 148 and an estimated time of travel (ETOT) column 150. Current kiosk column 142 lists all facility kiosks. Destination kiosk column 144 lists all facility kiosks separately for each one of the kiosks in column 142 (except for the associated kiosk in column 142). Thus, each of kiosks 26, 26c . . . 26z are listed for kiosk 26a1. Similarly, all of kiosks 26b through 26z are listed for kiosk 26a2, and so on.

Referring still to FIG. 4, map column 146, as the label implies, provides a separate graphical map for each one of the kiosk-kiosk combinations in columns 142 and 144. In column 146, exemplary maps are labeled "M (current kiosk identifier-destination kiosk identifier)". Thus, for instance, the map corresponding to current kiosk 26a1 and destination kiosk 26b in columns 142 and 144 is labeled M (26a1-26b). Each of the maps graphically shows facility features such as examination rooms, departments, hallways, etc., in plan format showing the location of the associated current kiosk and the destination kiosk and an optimal travel path to get from the current kiosk to the destination kiosk. Directions column 148 provides textual or, in some cases, verbal, directions for a patient for each one of the kiosk-kiosk combinations in columns 142 and 144. Each set of directions is identified by "D (current kiosk identifier-destination kiosk identifier)". Thus, the directions corresponding to kiosk 26a1 and kiosk location 26b are identified in column 148 by the label D (26a1-26b).

The ETOT column 150 indicates an estimated time of travel for each one of the kiosk-destination kiosk combinations in columns 142 and 144. For instance, the estimated time of travel between kiosk 26a1 and destination kiosk 26b is seven minutes in column 150 while the estimated time of travel between kiosk 26z and destination kiosk 26a1 is estimated to be 28 minutes.

In the interests of simplifying this explanation, various aspects of the inventive methods, processes and systems will be described in a context of an exemplary patient check in procedure wherein, referring once again to FIG. 2, patient Bruce Johnson (hereinafter "Mr. Johnson") 124 arrives at a medical facility on the morning of March 12 for his appointments at 8:00 a.m. and 8:45 a.m. with Dr. White and Dr. Jones, respectively. It will also be assumed that Mr. Johnson attempts to check in via kiosk 26a1. Moreover, it will be assumed that entry of patient identifying information is via a patient identification card 29 and card reader 19.

Figure 5:
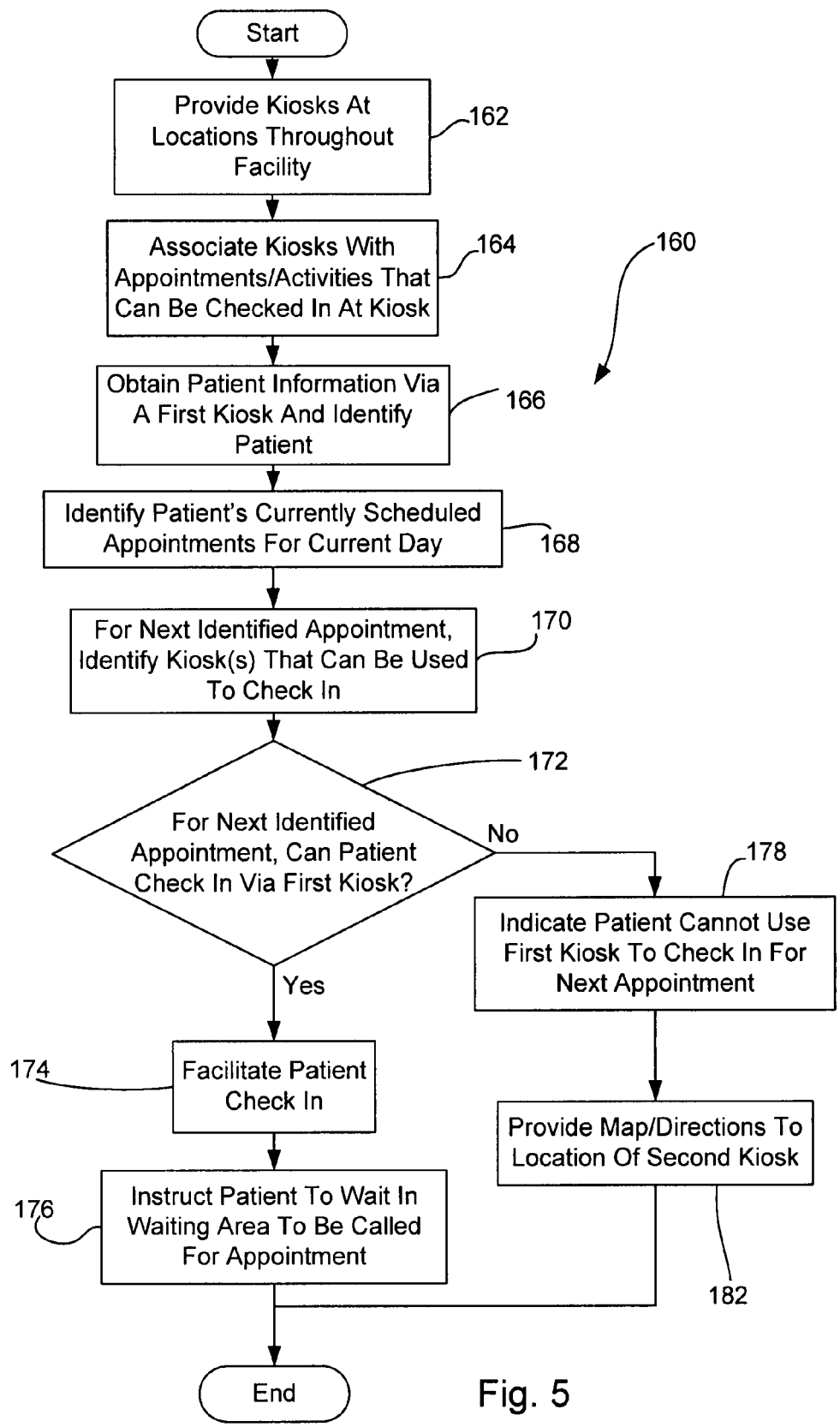

Referring now to FIG. 5, an exemplary method 160 that is consistent with at least some aspects of the present invention that may be performed by system 10 in FIG. 1 is illustrated whereby patients are guided to specific kiosks to check in for appointments at specific facility departments. Referring also to FIG. 1, at block 162 in FIG. 5, kiosks 26a1, 26a2, 26b, 26c, etc. are provided at locations throughout the facility. In the present example, it is assumed that kiosks 26a1 and 26a2 are provided proximate it each other and at a first location 25a, kiosk 26b is provided at location 25b and kiosk 26c is provided at location 25c. At block 164, each of the kiosks is associated with appointments or activities that can be checked in at the kiosk. An exemplary process for associating kiosks with appointments or activities that can be checked in at the kiosk is described below. At block 166, a patient 124 (see FIG. 1) uses a first kiosk 26a1 to enter patient identifying information which is used by server 22 to identify the patient that is using kiosk 26a1.

Figure 6:
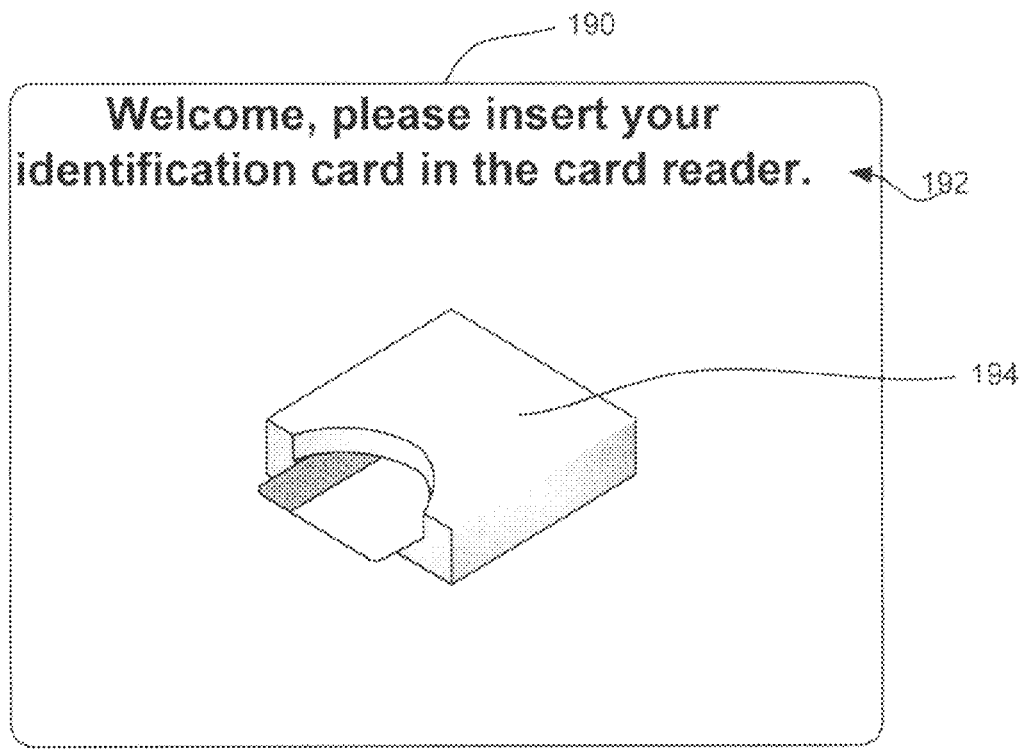
FIG. 6 is a screen shot that may be presented during a portion of the method of FIG. 5 via one of the kiosk displays shown in FIG. 1.

Referring also to FIG. 6, to obtain patient identifying information at block 166, server 22 causes a kiosk screen shot 190 to be presented via kiosk display 21. Exemplary screen shot 190 includes a welcoming and instruction statement 192 and a card reader image 194. In the present example, the instructions 192 and image 194 are meant to guide Mr. Johnson to slip his patient identification card into reader 19 so that server 22 can obtain identifying information from Mr. Johnson.

Referring to FIGS. 1, 2 and 5, after server 22 identifies Mr. Johnson, server 22 accesses patient appointments database 76 and identifies Mr. Johnson's scheduled appointments for the current day. As shown in FIG. 2, current appointments for Mr. Johnson 124 include his follow up visit for a hernia operation with Dr. White at 8:00 a.m. and his chest pain examination with Dr. Jones at 8:45 a.m.

At block 170, server 22 identifies kiosks that can be used to check in Mr. Johnson's next appointment (i.e., the 8:00 a.m. appointment) for the current day. To this end, server 22 again accesses the patient appointments database 76 and identifies the department in column 108 at which the appointment in column 105 is to take place. In FIG. 2, Mr. Johnson's hernia operation follow up (i.e., the next appointment) is to take place at department 27c. In addition, after identifying the appointment department for the next appointment via database 76, server 22 accesses kiosk functionality database 78 and identifies, for the department at which Mr. Johnson's next appointment is to occur, each instance of a department identifier in column 116 and then identifies the kiosk in column 112 that corresponds to the department instance in column 116. Thus, for example, for Mr. Johnson's hernia operation follow up that is to occur in department 27c as indicated in column 108, server 22 identifies instance 115 of department identifier 27c in column 116 and associated kiosk 26c in column 112 to determine that kiosk 26c can be used by Mr. Johnson to check in for his 8:00 a.m. hernia operation follow up with Dr. White.

Referring still to FIGS. 1 and 5, at block 172, for Mr. Johnson's next appointment identified at block 168, server 22 determines whether or not Mr. Johnson can check in via the kiosk he is currently using (i.e., kiosk 26a1). Consistent with the example above, because Mr. Johnson's 8:00 a.m. appointment is to occur at department 25c, Mr. Johnson cannot check in for that appointment at kiosk 26a1. For the 8:00 a.m. appointment that has to be checked in via kiosk 26c, control passes to block 178 where server 22 indicates, via kiosk display 21, that Mr. Johnson cannot use the kiosk he is currently using to check in for his 8:00 a.m. appointment. At block 182, server 22 accesses way finder database 80 (see also FIG. 4) and identifies a map and/or directions in column 146 or 148, respectively, for instructing Mr. Johnson on the best way to travel from the kiosk Mr. Johnson is currently using 26a1 to one of the kiosks that was identified at block 170 that can be used to check in for the 8:00 a.m. appointment. The map and/or directions are provided at block 182.

In addition, at block 170 server 22 may determine that kiosk 26a1 can be used to check in Mr. Johnson's 8:45 a.m. appointment and provide notice to Mr. Johnson that kiosk 26a1 can be used for that purpose. Here, however, because Mr. Johnson has to travel to location 25c for his first appointment prior to the 8:45 a.m. appointment, in at least some embodiments, server 22 will not allow check in for the 8:45 a.m. appointment until the 8:00 a.m. appointment has been completed. By refusing check in for the 8:45 a.m. appointment prior to completion of the 8:00 a.m. appointment, the system will force Mr. Johnson to travel back to location 25a and kiosk 26a1 (or kiosk 26a2 in the present example) to check in for the 8:45 a.m. appointment.

Figure 7:
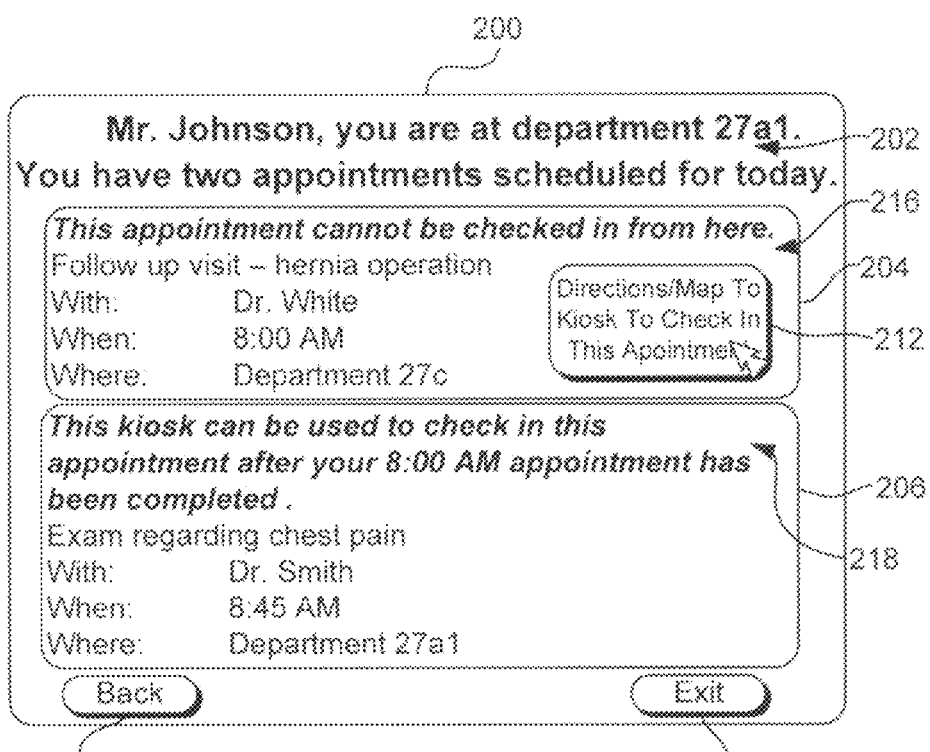
FIG. 7 is a kiosk screen shot that may be presented during one of the process steps shown in FIG. 5 to indicate to a patient that the patient cannot use the current kiosk to check in for an appointment.

Referring now to FIG. 7, an exemplary screen shot 200 that may be presented via kiosk display 21 is shown that is consistent with the example above where Mr. Johnson uses kiosk 26a1 to attempt to check in for both of his 8:00 a.m. and 8:45 a.m. appointments. Screen shot 200 includes an informational header 202 that lets Mr. Johnson know his location (e.g., department 27a1) and that he has two appointments scheduled for the current day. Mr. Johnson's 8:00 a.m. appointment is described in a first appointment field 204 and his second appointment is described in a second appointment field 206. In addition to describing the first appointment, field 204 also includes a warning message 216 indicating that Mr. Johnson's 8:00 a.m. appointment cannot be checked in from the current kiosk. In addition, a selectable DIRECTIONS/MAP TO KIOSK TO CHECK IN THIS APPOINTMENT button 212 is presented in field 204 which, as the label implies, can be selected to obtain directions and/or a map to kiosk 26c to check in for the 8:00 a.m. appointment.

Field 206 describes the 8:45 a.m. appointment and includes information 218 indicating that, while current kiosk 26a1 can be used to check in the 8:45 a.m. appointment, that the 8:45 a.m. appointment cannot be checked-in until after the 8:00 a.m. appointment has been completed. This precautionary information ensures that Mr. Johnson will not wait at location 25c for his 8:45 a.m. appointment and instead will have to return to location 25a to check in for the second appointment.

In addition to fields 204 and 206, screen shot 200 includes a BACK icon 208 and an EXIT icon 210. BACK icon 208 is selectable to move to a previously displayed screen shot (e.g., 190 in the present example). EXIT icon 210 is selectable to exit or log off kiosk 26a1. Hereinafter, BACK and EXIT icons that appear on exemplary screen shots operate in a fashion similar to that described here and therefore they will not again be described in detail.

Figure 8:
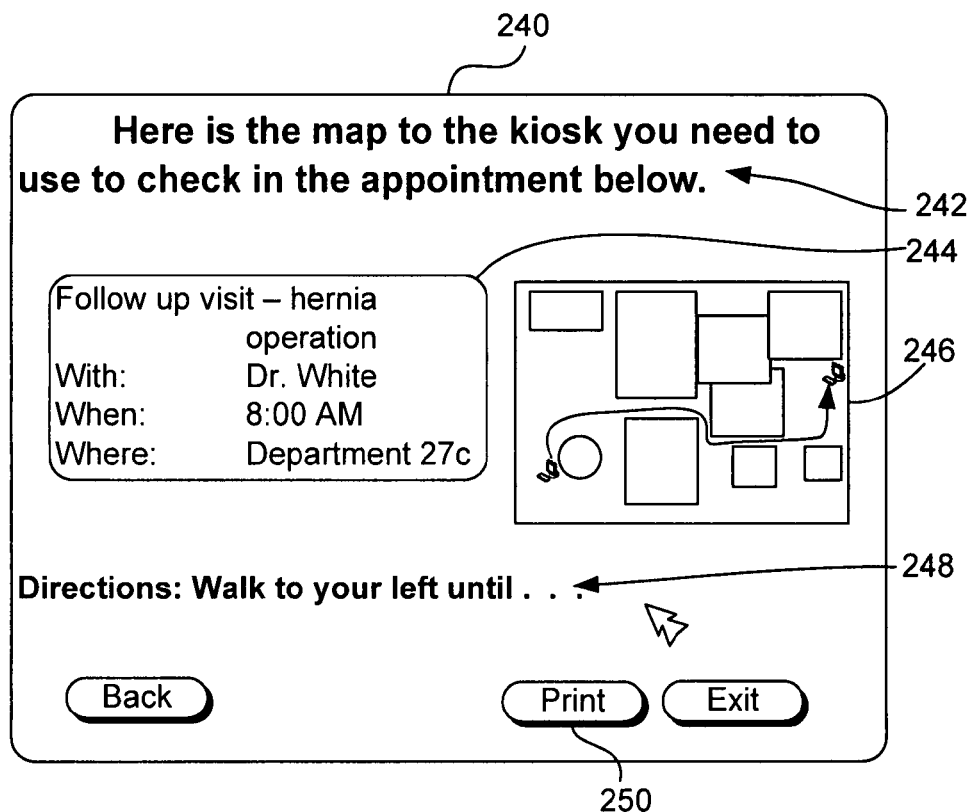
FIG. 8 is a kiosk screen shot that may be presented during one of the process steps shown in FIG. 5 for providing a map or directions to a patient to find a check in kiosk for checking in for specific appointments.

Referring still to FIG. 7, when Mr. Johnson selects icon 212, the screen shot 240 shown in FIG. 8 may be provided. Screen shot 240 includes information 242 indicating that a map appears below for guiding Mr. Johnson to the kiosk that Mr. Johnson has to use to check in for his 8:00 a.m. appointment. In addition, screen shot 240 includes information 244 clearly specifying the appointment and map 246 which can be viewed via screen 21. Exemplary textual directions 248 are also included in screen shot 240. A PRINT icon 250 is provided near the bottom of screen shot 240 which may be selected to print the map 246, directions 248 and/or other screen shot 240 information.

Figure 9:
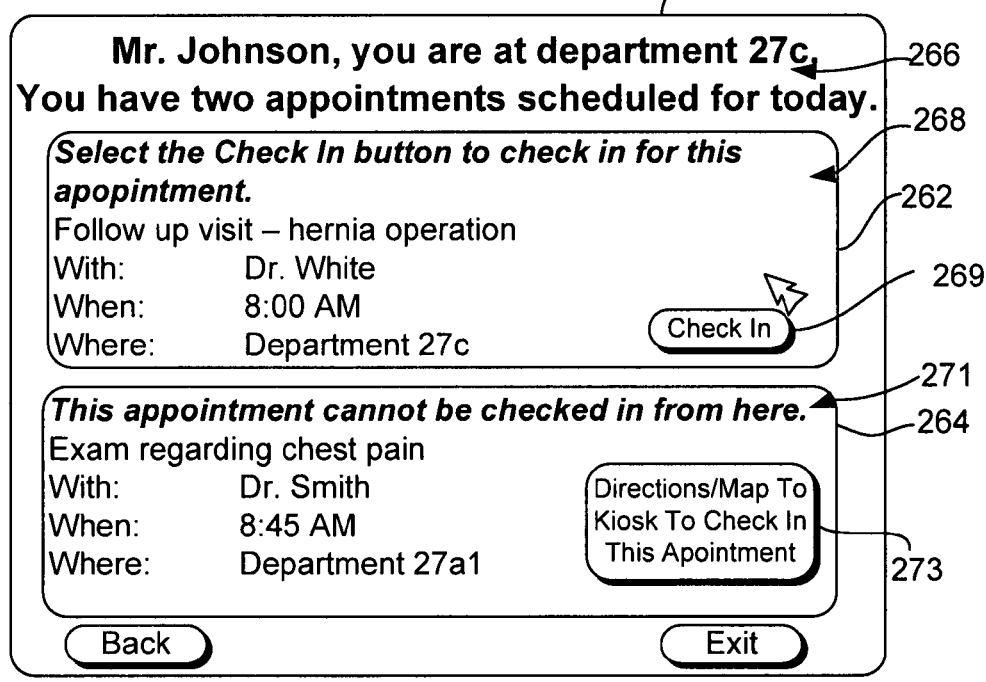
FIG. 9 is a kiosk screen shot that may be presented to a patient during one the process steps of FIG. 5 to facilitate patient check in for an appointment.

Now assume that Mr. Johnson prints out directions from kiosk 26a1 to kiosk 26c (i.e., to location 25c) and travels to kiosk 26c. After Mr. Johnson logs on to kiosk 26c, server 22 performs the FIG. 5 process again and this time generates screenshot 260 shown in FIG. 9. Screen shot 260 includes information 266 indicating Mr. Johnson's location as well as appointment fields 262 and 264 for Mr. Johnson's 8:00 a.m. and 8:45 a.m. appointments, respectively. Now field 262 includes instructions 268 guiding Mr. Johnson to select a CHECK IN icon 269 to check in for his 8:00 a.m. appointment at department 27c. Field 264 includes a warning that the 8:45 a.m. appointment cannot be checked-in at kiosk 26c and an icon 273 for receiving directions to a kiosk (e.g., kiosk 26a1) that can be used to check in for the 8:45 a.m. appointment.

When Mr. Johnson selects icon 269 to check in, referring to block 174 in FIG. 5, control passes to block 176 where server 22 instructs Mr. Johnson to wait in the waiting area associated with department 27c.

Figure 10:
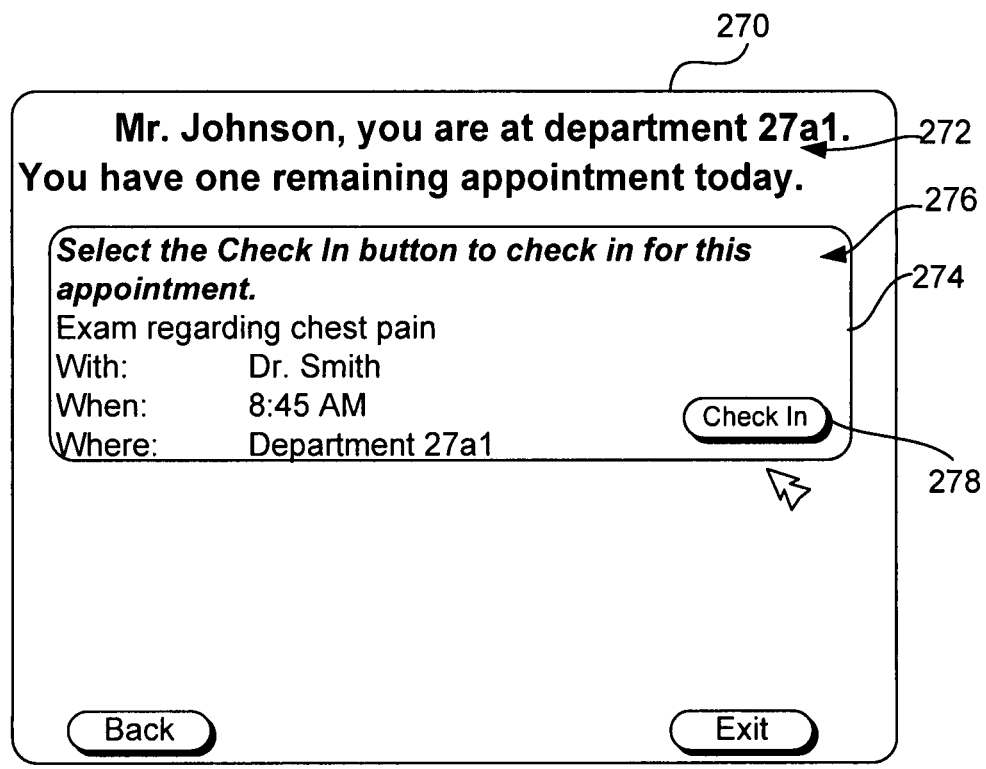
FIG. 10 is a kiosk screen shot that may be presented during one of the process steps shown in FIG. 5 to facilitate patient check in of another appointment.

Next, assume that after the 8:00 a.m. appointment is completed Mr. Johnson travels back to kiosk 27a1 and logs on to register for his 8:45 a.m. appointment. Now, because the 8:00 a.m. appointment has been completed, server 22 presents screen shot 270 in FIG. 10 that confirms 272 that Mr. Johnson only has one more appointment and that provides a single appointment field 274 describing the 8:45 a.m. appointment and including instructions 276 and a CHECK IN icon 278.

In at least some embodiments it is contemplated that, in addition to providing warnings and directions to specific check in kiosks, server 22 may use the estimated times of travel in column 150 of way finder database 80 (see FIG. 4) to identify the estimated amount of time for a patient to travel from a currently used kiosk to the location at which an appointment is to occur and may provide that estimated time to the patient. To this end, referring now to FIG. 11, a sub-process 280 that may be added to process 160 in FIG. 5 is shown. Referring also to FIGS. 1 and 5, after block 178, control may pass to block 282 in FIG. 11 where server 22 uses way finder database 80 and, more specifically, information in column 150, to estimate the travel time between the currently used kiosk (i.e., first kiosk) and the kiosk that has to be used to check in a specific appointment (i.e., a second kiosk). In the present example, server 22 estimates the travel time from kiosk 26a1 to kiosk 26c which, column 150 indicates is 16 minutes. At block 284, server 22 indicates the estimated travel time to Mr. Johnson via display 21. In addition, at block 284, server 22 may provide information to a receptionist via receptionist's terminal 90 indicating that Mr. Johnson has attempted to check in for his 8:00 a.m. appointment via kiosk 26a1 and the estimated travel time for Mr. Johnson from kiosk 26a1 to kiosk 26c. Where information is provided to a receptionist, the receptionist may take steps to expedite other patients' appointments when appropriate or to fill in Dr. White's time with another patient if appropriate.

Figure 11:
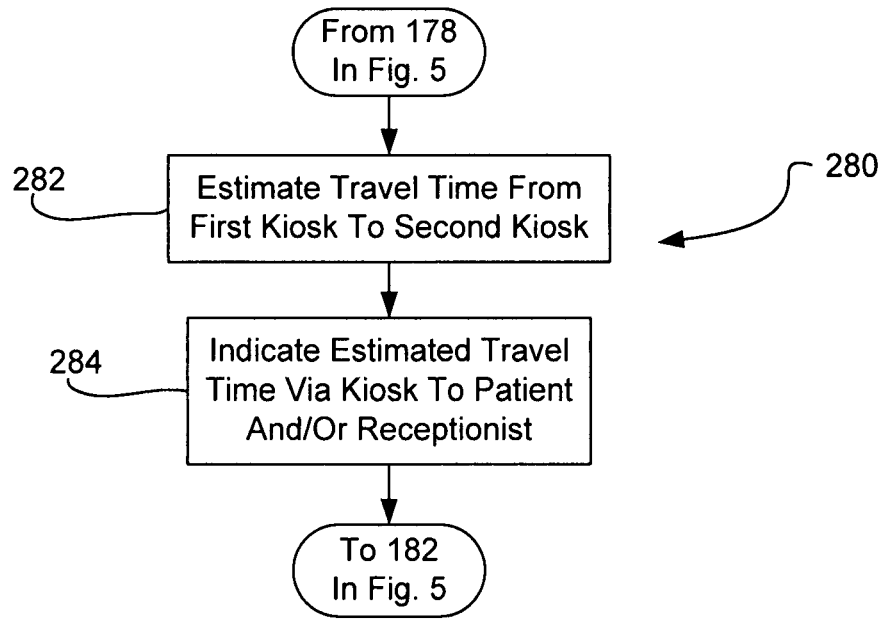
FIG. 11 is a flow chart illustrating a subprocess that may be added to the process shown in FIG. 5 so that an estimated travel time for a patient can be provided.
Figure 12:
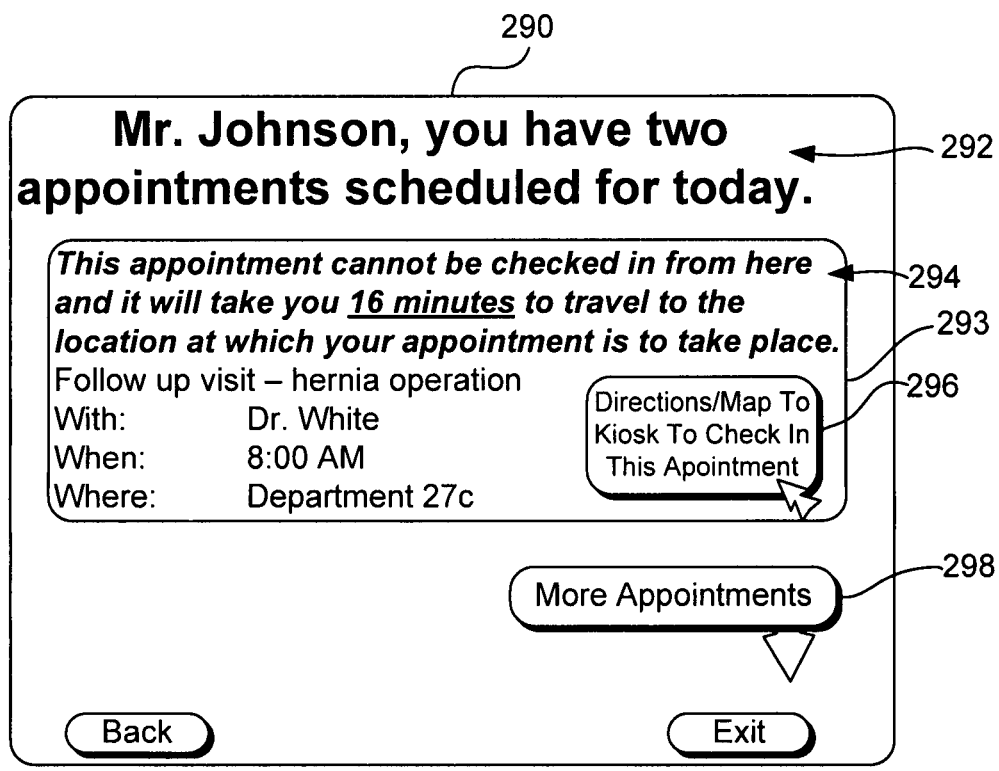
FIG. 12 is a kiosk screen shot that may be presented during one of the process steps shown in FIG. 11 to indicate an estimated travel time from a kiosk to a location at which an appointment is to occur.

Referring now to FIG. 12, an exemplary screen shot 290 is shown for providing information to Mr. Johnson in the present example including an estimated travel time from kiosk 26a1 to kiosk 26c. To this end, screen shot 290 includes field 293 associated with Mr. Johnson's 8:00 a.m. appointment which includes a warning 294 that the appointment cannot be checked in using kiosk 26a1 and that it will take 16 minutes for Mr. Johnson to get from his current location to the location at which his appointment is to occur. Once again, a button 296 is provided that can be selected to receive a map or instructions from Mr. Johnson's current location to the location at which his appointment is to occur. In FIG. 11, a MORE APPOINTMENTS button 298 is provided that can be selected to view other appointments (i.e., the 8:45 a.m. appointment) Mr. Johnson has on the current day.

In at least some embodiments it is contemplated that, in addition to identifying the amount of time required to travel from a current location to the location at which an appointment is to occur, server 22 may be programmed to determine whether or not, given the estimated travel time, a patient will miss his appointment and, where a patient will likely miss his appointment, server 22 may be programmed to cancel the appointment. In at least some embodiments where server 22 cancels an appointment, the server may also be programmed to facilitate a rescheduling of the appointment when appropriate.

Figure 13:
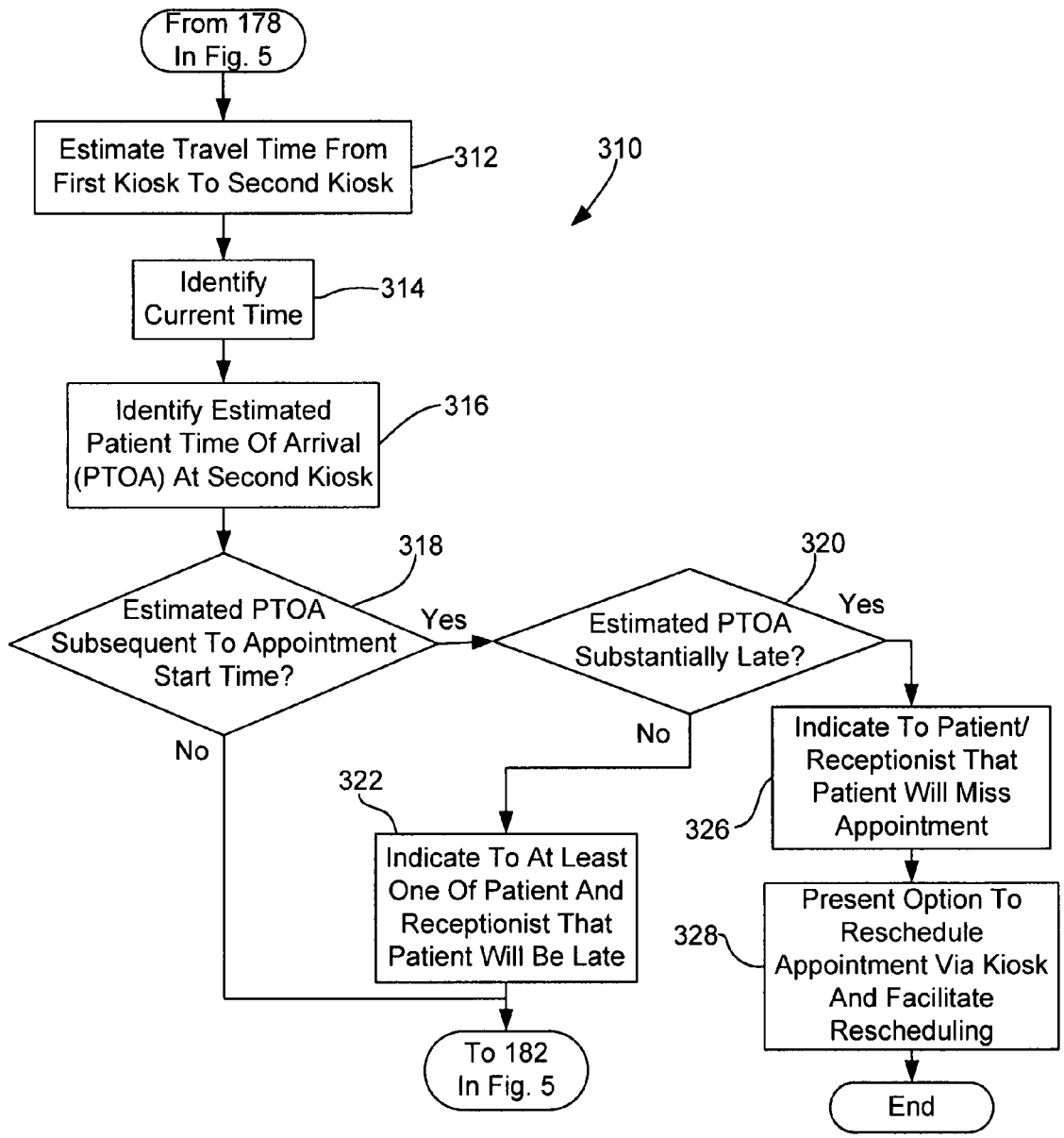
FIG. 13 is a flow chart illustrating a subprocess that may be added to the process of FIG. 5 for estimating tardiness of a patient for an appointment and for canceling the appointment when appropriate.

Referring now to FIG. 13, an exemplary sub-process 310 that may be added to process 160 in FIG. 5 is illustrated for canceling and rescheduling a missed appointment. Referring also to FIGS. 1 and 5, after block 178 in FIG. 5, control may pass to block 312 in FIG. 13 where server 22 estimates the travel time from the currently used kiosk to the kiosk that has to be used to check in an appointment. Again, in the present example, server 22 estimates the travel time from kiosk 26a1 to kiosk 26c as being 16 minutes. At block 314 server 22 identifies the current time. At block 316, server 22 identifies the estimated patient time of arrival (PTOA) at kiosk 26c. Estimating the PTOA is as simple as adding the estimated travel time from kiosk 26a1 to kiosk 26c to the identified current time.

Referring still to FIGS. 1 and 13, at block 318, server 22 determines whether or not the estimated PTOA is subsequent to the start time of the appointment. Thus, in the present example, server 22 determines whether or not the estimated PTOA is subsequent to the 8:00 a.m. start time for Mr. Johnson's first appointment. Where the estimated PTOA time is not subsequent to the start time of the appointment, control passes back to block 182 in FIG. 5 where server 22 provides a map and directions for finding kiosk 26c.

Referring still to FIGS. 1 and 13, where the estimated PTOA is subsequent to the appointment start time, control passes to block 320 where server 22 determines whether or not the estimated PTOA time is substantially late. Here, substantially late may mean that the estimated PTOA time is subsequent to an end time for the appointment. In other cases, substantially late may mean that the estimated PTOA time is later than one-half the anticipated duration of the appointment. Other measures for the qualifier "substantially late" are contemplated. Where the estimated PTOA time is not substantially late, control passes to block 322 where server 22 indicates to the patient and, perhaps, to a receptionist via terminal 90, that the patient will be late for the appointment after which control passes back to block 182 in FIG. 5.

Referring still to FIGS. 1 and 13, where the estimated PTOA time is substantially late, control passes to block 326. At block 326, server 22 indicates that the patient will miss his appointment. Here, the missed appointment indication is provided to both the patient and the receptionist. At block 328, an option to reschedule the missed appointment is presented to Mr. Johnson via display 21 and the appointment may be rescheduled. Here, to determine rescheduling options, server 22 accesses resource schedule database 82 (see once again FIG. 1) where server 22 can determine which resources are required for the appointment, access, resource schedules and use the accessed schedules to identify rescheduling options. The rescheduling options may be provided to Mr. Johnson and one may be selected to reschedule the missed appointment. After block 328 the process ends.

Figure 14:
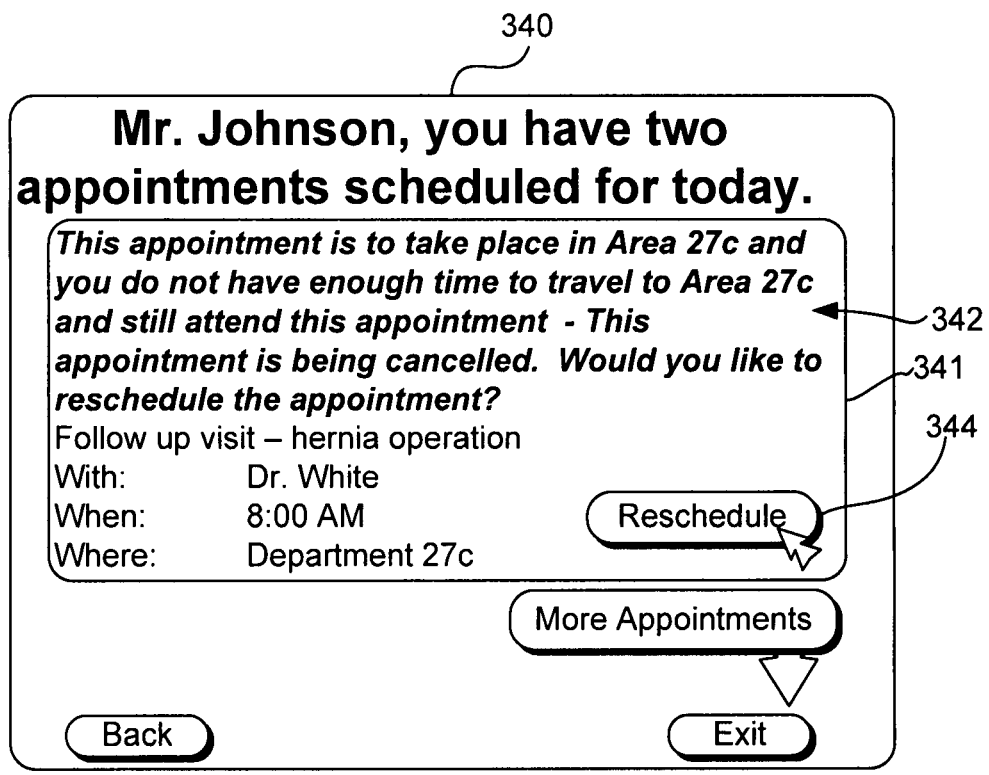
FIG. 14 is a kiosk screen shot that may be presented during one of the process steps shown in FIG. 13 to indicate that the patient will miss an appointment and to facilitate rescheduling of the appointment.

Referring now to FIG. 14, an exemplary screen shot 340 that may be presented via display 21 when an appointment has been missed is illustrated. Screen shot 340 includes an appointment field 341 that includes a missed appointment notice 342 as well as a RESCHEDULE button 344. Where button 344 is selected, server 22 commences a rescheduling procedure.

Figure 15:
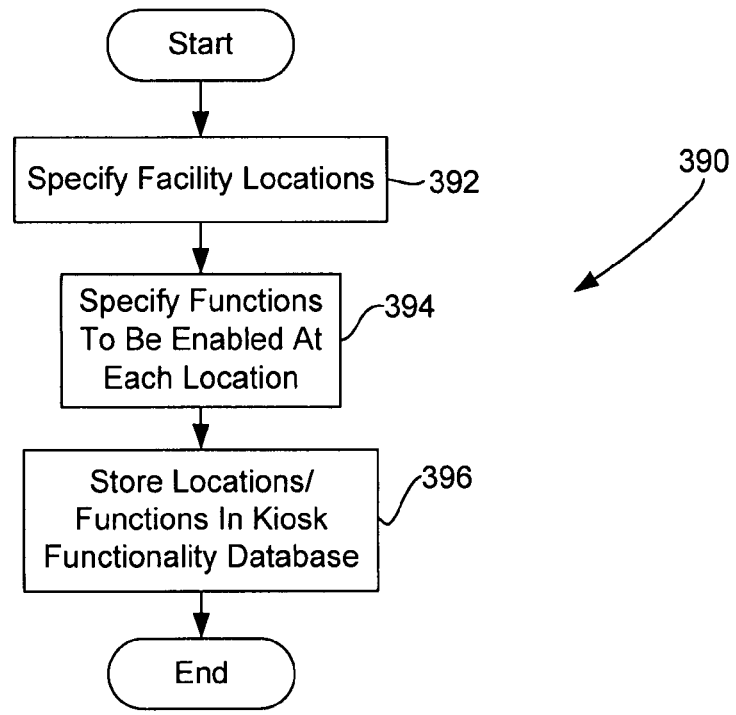
FIG. 15 is a flow chart illustrating a process by which kiosk functions are associated with facility locations.
Figure 16:
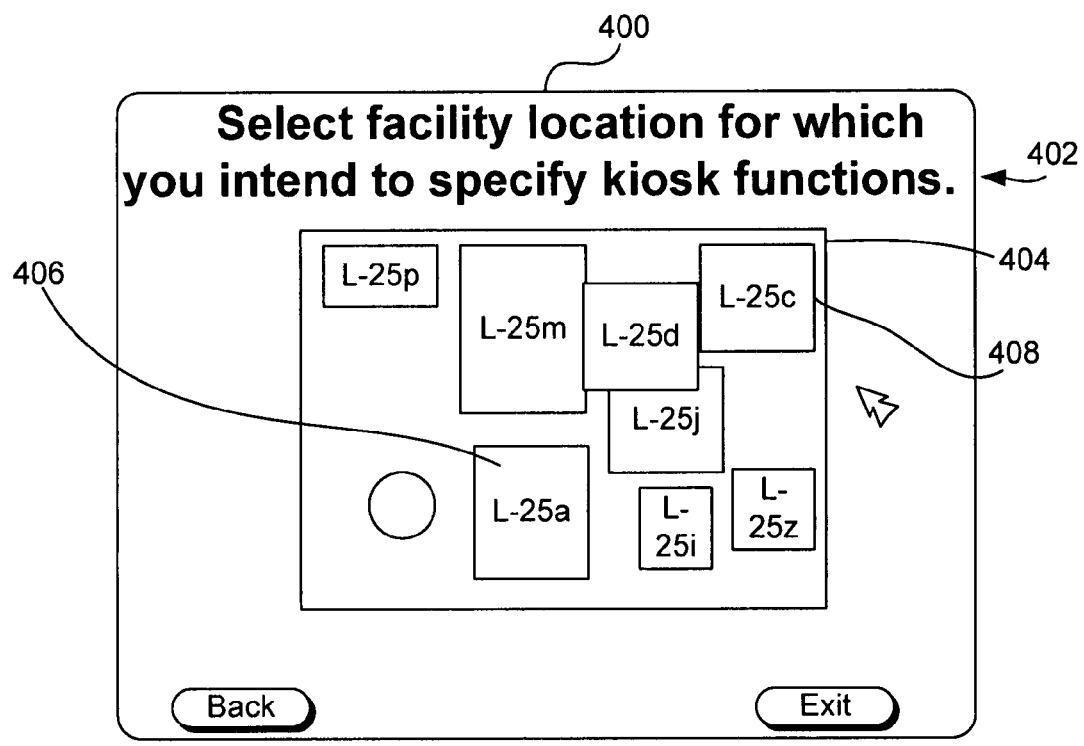
FIG. 16 is a screen shot that may be presented to a system administrator during one of the process steps shown in FIG. 15 for selecting a facility location for which kiosk functions are to be specified.

Referring now to FIG. 15, an exemplary method 390 for associating facility locations with specific functions that can be performed by kiosks at those locations is illustrated. Referring also to FIG. 1, receptionist/administrator terminal 90 may be used as an interface to communicate with server 22 and carry out method 390. At block 392, server 22 provides tools via terminal 90 that can be used by an administrator or the like to specify facility locations. Referring also to FIG. 16, an exemplary screen shot 400 that may be presented via terminal 90 for selecting facility locations is shown. Screen shot 400 includes instructions 402 indicating that the user should select a facility location for which kiosk functions are to be specified. In addition, screen shot 400 includes a graphical map 404 where different facility locations are identified by labels L-25 followed by small case letters. Thus, for instance, location 25a in FIG. 1 is identified by label L-25a (see 406), location 25c in FIG. 1 is identified by label L-25c (see 408), etc. Here, each of the labels is selectable via a mouse-controlled cursor and, when selected, server 22 presents a screen shot 420 that allows the administrator to specify various functions that may be performed by a kiosk associated with or located in the selected location.

Figure 17:
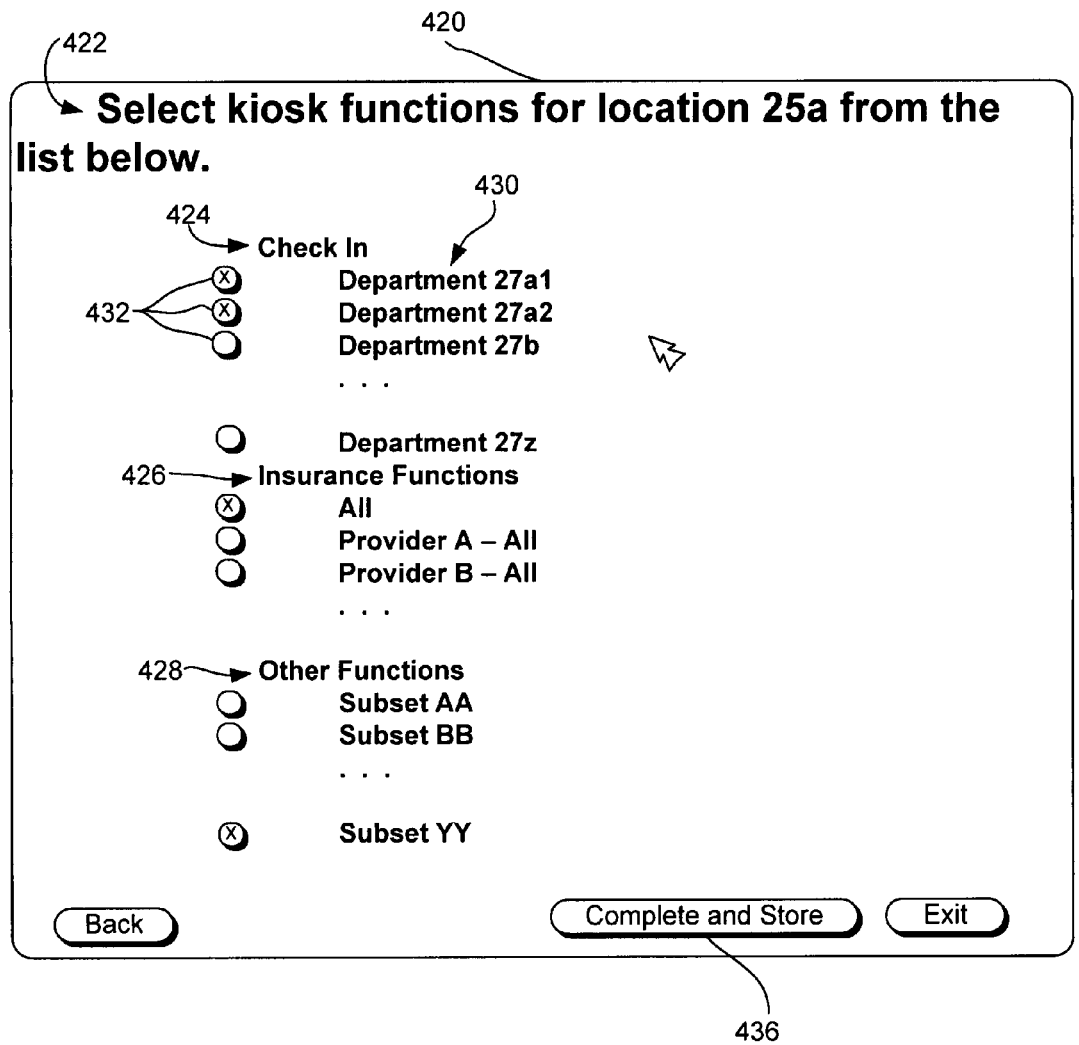
FIG. 17 is a screen shot that may be presented to a system administrator via one of the process steps shown in FIG. 15 for specifying functions to be enabled for a specific location.

Referring still to FIGS. 1 and 15 and also to FIG. 17, at block 394, the administrator specifies kiosk functions to be enabled at each location. In this regard, exemplary screen shot 320 in FIG. 17 includes instructions that instruct the administrator to select kiosk functions for the location selected via screen shot 400 in FIG. 17. Here, it is assumed that the administrator selected location 406 (i.e., location L-25a) in FIG. 15 and therefore screen shot 420 can be used to select kiosk functions for location 25a (see also FIG. 1).

Screen shot 420 also includes various types of functions that may be performed via kiosk associated with location 25a including check in functions 424, insurance functions 426 and other functions 428. Under the check in function section 424, screen shot 420 lists each of the facility departments in a list 430 and, for each department in the list 430, provides a binary button, three of which are collectively identified by numeral 432. Each button 432 may each be individually selected to indicate that check in should be allowed via kiosks at location 25a for the corresponding department. Consistent with the kiosk functionality database 78 shown in FIG. 3, it can be seen in FIG. 17 that, for location 25a, check in is allowed for each of departments 27a1 and 27a2.

Referring still to FIG. 17, insurance functions section 426, as the label implies, allows an administrator to customize insurance functions that can be facilitated via kiosks associated with location 25a. Exemplary insurance function options include an "All" option, a "Provider A-All" option and a "Provider B-All" option. Here, it is contemplated that each of the insurance function options would be distinct and allow different functionality. Thus, the "All" option would mean that a full suite of insurance functionality is provided while the "Provider-A-All" option may mean that all insurance functions for an insurance company A are to be supported while only limited functionality is to be provided in the case of other insurers.

The other functions sections 428 allows the administrator to specify other kiosk functions that may be performed via kiosks associated with location 25a. For example, another function listed in section 428 may include a check out function that enables a patient to check out after employment has been completed. Other functions may also include scheduling functions, functions that allow a patient to update personal information stored by the facility, information that allows a user to access billing related matters, rescheduling functions, functions related to notices to patient, etc. After an administrator has specified kiosk functions via binary buttons 432, the administrator can select COMPLETE AND STORE button 436 to store the specified kiosk functions in the kiosk functionality database 78 (see FIG. 3). The exemplary database 78 in FIG. 3 stores the locations and related functions in columns 114, 116, 188 and 120.

Figure 18:
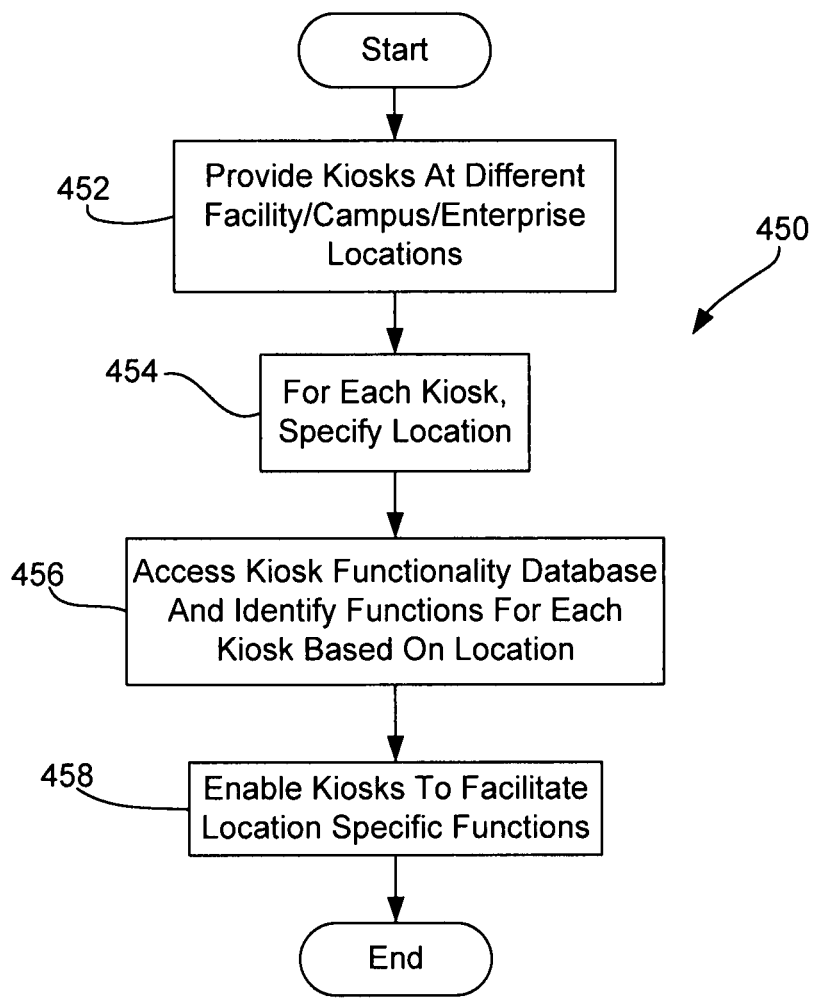
FIG. 18 is a flow chart illustrating a process by which a system administrator specifies a kiosk location and the server of FIG. 1 assigns functionality to the kiosk based on the kiosk's location.
Figure 19:
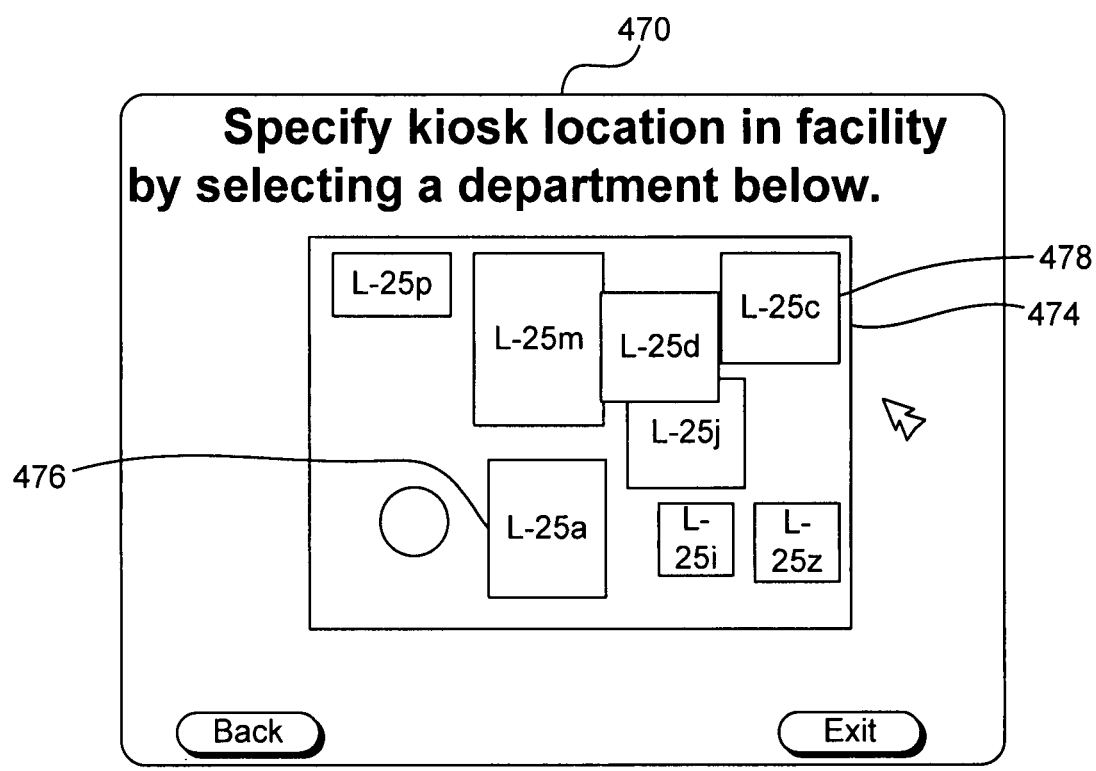
FIG. 19 is a screen shot that may be presented to a system administrator during one of the process steps shown in FIG. 18 for specifying a kiosk location.

Referring now to FIG. 18, a process 450 is illustrated for configuring specific kiosks within a facility. Here, process 450 may be performed using the receptionist/administrator terminal 90 in the alternative, may be performed using specific kiosks (e.g. 26a1, 26b, etc.). Referring also to FIG. 1, kiosks 26a1, 26a2, 26b, etc., are provided at different locations throughout the facility at block 452. At block 454, an administrator uses a specific kiosk (e.g., 26a1) to access commissioning tools that allow the administrator to identify the location of the kiosk. To this end, see exemplary screen shot 470 in FIG. 19 that includes a facility map 474 where different locations/zones 476, 478, etc., are shown. In this example a kiosk location can be specified by selecting a map location via the mouse controlled cursor.

At block 456, server 22 accesses kiosk functionality database 78 in FIG. 3 and identifies functions in columns 116, 118 and 120 associated with the specified location. At block 458, server 22 enables the kiosk to facilitate the functions associated with the location. To associate a kiosk with functions a kiosk identifier is added to column 112 in database 78.

In at least some embodiments kiosk location within a facility may be determined automatically either via the actual physical location on network 24 to which the kiosk is linked or via wireless location determining methods where the kiosk includes a wireless transceiver (see 41 in FIG. 1) and wireless access points (see 169a, 169b, etc) are located throughout the facility. Triangulation and other statistical methods for wirelessly determining device location within a facility are well known. Thus, in some embodiments server 22 and the access points may form a wireless location determining system. Here it is contemplated that when a kiosk is moved within the facility, kiosk functionality may change automatically as a function of kiosk location. Thus, for instance, where kiosk 26a1 is at location 25a, kiosk 26a1 may be useable to check in for appointments for either of departments 27a1 or 27a2 but not for department 27c appointments and when kiosk 26a1 is at location 25c, kiosk 26a1 may be usable to check in for department 27c appointments but not for department 27a1 and 27a2 appointments.

Furthermore, where kiosks 26a1, 26a2, etc., are wireless, in some embodiments it is contemplated that each of the kiosks may take the form of a personal digital assistant (PDA) or portable wireless communications device (WCD) or the like that the patient can carry around within the facility or on a providers campus. To this end, see hand held device 30 in FIG. 1. Here, it is contemplated that location of device 30 can be determined essentially in real time as device 30 is moved about in the facility and location specific check in functions can be facilitated as described above. Moreover, in at least some embodiments, it is contemplated that device 30 may be a patient's own PDA, a cell phone, a Blackberry device, etc. and location specific check in may be facilitated thereby.

One or more specific embodiments of the present invention have been described above. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Thus, the invention is to cover all modifications, equivalents, and alternatives falling within the spirit and scope of the invention as defined by the following appended claims. For example, while system 10 in FIG. 1 is shown as having a single receptionist/administrator terminal 90, in some embodiments multiple terminals 90 may be provided, at least one terminal for each area 25a, 25b, etc., or at least one terminal for each department 27a1, 27a2, etc. Where each department includes a terminal 90, notice of late and/or canceled appointments may be provided to the terminal 90 at the department affected. In addition, in at least some embodiments kiosk functionality may only be controllable/settable locally via department terminals. Thus, for instance, it may be that only the department terminal 90 associated with department 27a can be used to select and/or change functions performed by kiosk associated with location 25a (i.e., kiosks 26a1 and 26a2).

As another example, while the system described above works well where kiosks are located throughout a facility, in at least some embodiments it is contemplated that more conventional check in resources (e.g., a receptionist) may be located at some facility locations/departments. In these cases the location limited kiosks described above would operate in a similar fashion to that described above to direct patients to whatever check in resources are available proximate the correct location of an appointment. Thus, a kiosk may present instructions to prompt a patient to travel to another location when appropriate.

What is claimed is:

1. A method for helping a client check in for a scheduled activity wherein at least first and second subsets of activities occur proximate first and second locations, respectively, the method comprising the steps of:
providing a check in resource at the second location for checking clients in for the second subset of activities;
associating at least a first electronic kiosk with the first subset activities;
positioning the first kiosk at the first location for use by clients to check in for first subset activities;
via the first kiosk, receiving identifying information from a first client;
identifying at least a first currently scheduled activity for the first client;
determining that the first currently scheduled activity is one of the second subset activities; and
via the first kiosk, indicating that the first client cannot check in for the first currently scheduled activity via the first kiosk.

2. The method of claim 1 further including the step of, after determining that the first currently scheduled activity is one of the second subset activities, indicating that the first client must check in for the first currently scheduled activity at the second location.

3. The method of claim 2 further including the steps of identifying an estimated travel time for the first client to travel from the first location to the second location and presenting the estimated travel time to the first client via the kiosk.

4. The method of claim 3 further including the step of, after determining that the first currently scheduled activity is one of the second subset activities, providing notice to a receptionist indicating that the first client is at the first location.

5. The method of claim 3 wherein the first activity is scheduled to commence at a first time, the method further including the steps of using the current time and the estimated travel time to identify a predicted arrival time of the first client at the second location and, when the predicted arrival time is subsequent to the first time, providing notice to a receptionist.

6. The method of claim 3 wherein the first activity is scheduled to commence at a first time, the method further including the steps of using the current time and the estimated travel time to identify a predicted arrival time of the first client at the second location and, when the predicted arrival time is subsequent to the first time, providing notice to the first client via the first kiosk.

7. The method of claim 6 wherein at least a first resource is required to perform the first activity, the method further including the steps of, when the predicted arrival time is substantially subsequent to the first time, indicating that the client should reschedule the first activity for a time subsequent to the first time.

8. The method of claim 6 wherein at least a first resource is required to perform the first activity, the method further including the steps of, when the predicted arrival time is substantially subsequent to the first time, accessing a resource schedule for the first resource and attempting to identify an open schedule time slot subsequent to the first time for performing the first activity for the first client.

9. The method of claim 8 further including the steps of, when at least one open schedule time slot is identified, presenting the time slot to the first client via the kiosk and facilitating rescheduling of the first activity.

10. The method of claim 2 further including the step of providing instructions via the kiosk directing the client from the first location to the second location.

11. The method of claim 10 wherein the step of providing instructions includes providing a graphical map via the kiosk.

12. The method of claim 11 wherein the kiosk includes a printer and wherein the step of providing a graphical map includes printing out a hard copy of the graphical map.

13. The method of claim 1 wherein the first and second locations are in a single facility.

14. The method of claim 1 wherein the step of providing check in resources at the second location includes providing a second electronic kiosk at the second location for checking clients in for second subset activities.

15. The method of claim 14 further including the steps of:
via the second kiosk, receiving identifying information from a second client;
identifying at least a first currently scheduled activity for the second client;
determining that the first currently scheduled activity for the second client is one of the first subset activities; and
via the second kiosk, indicating that the second client must check in for the first currently scheduled activity for the second client at the first location.

16. The method of claim 15 wherein at least a third subset of activities occur proximate a third location, the method further including the steps of providing at least a third electronic kiosk at the third location for checking clients in for third subset activities, when the first currently scheduled activity is one of the third subset activities, indicating via the first kiosk that the first client must check in for the first currently scheduled activity at the third location and, when the first currently scheduled activity for the second client is one of the third subset activities, indicating via the second kiosk that the second client must check in for the first currently scheduled activity for the second client at the third location.

17. The method of claim 1 further including the steps of:
via the first kiosk, identifying at least a second currently scheduled activity for the first client;
determining that the second currently scheduled activity for the first client is one of the first subset activities; and
via the first kiosk, enabling the first client to check in for the second currently scheduled activity via the first kiosk.

18. The method of claim 1 wherein the clients are patients and wherein the kiosks are associated with a medical facility.

19. The system of claim 1 wherein the clients are patients and wherein the interface devices are associated with a medical facility.

20. A method for helping a client check in for a scheduled activity wherein first through Nth subsets of activities occur proximate first through Nth locations, respectively, the method comprising the steps of:
associating first through Nth electronic kiosks with the first through Nth subsets of activities, respectively;
positioning the first through Nth kiosks at the first through Nth locations for use by clients to check in for first through Nth subsets of activities, respectively;
via at least the first kiosk:
receiving identifying information from a first client;
identifying at least a first currently scheduled activity for the first client;
determining that the first currently scheduled activity is one of an Xth subset activities associated with an Xth kiosk and that occur proximate an Xth location where X is between 2 and N; and
indicating that the first client must check in for the first currently scheduled activity at the Xth location.

21. The method of claim 20 further including the steps of identifying an estimated travel time for the first client to travel from the first location to the Xth location and presenting the estimated travel time to the first client via the first kiosk.

22. The method of claim 21 wherein the first activity is scheduled to commence at a first time, the method further including the steps of using the current time and the estimated travel time to identify a predicted arrival time of the first client at the Xth location and, when the predicted arrival time is subsequent to the first time, providing notice to the first client via the first kiosk.

23. The method of claim 21 further including the step of providing instructions via the kiosk directing the client from the first location to the second location.

24. The method of claim 20 further including the steps of, via the first kiosk:
identifying at least a second currently scheduled activity for the first client; determining that the second currently scheduled activity for the first client is one of the first subset activities; and
enabling the first client to check in for the second currently scheduled activity via the first kiosk.

25. The method of claim 20 further including the step of, after determining that the first currently scheduled activity is one of an Xth subset activities associated with an Xth kiosk and that occur proximate an Xth location where X is between 2 and N, indicating that the first client must check in for the first currently scheduled activity at the Xth location.

26. A system for helping a client check in for a scheduled activity wherein at least first and second subsets of activities occur proximate first and second locations, respectively, the system comprising:
a database storing currently scheduled appointments for clients;
a processor;
a check in resource located at the second location for checking clients in for the second subset of activities;
a first interface device associated with the first subset activities and located at the first location for receiving client identifying information and providing information to clients and also for use by clients to check in for first subset activities;
a processor programmed to, when client identifying information is provided via the first interface device:
identify the client as a first client;
identify at least a first currently scheduled activity for the first client;
determine that the first currently scheduled activity is one of the second subset activities; and
via the first interface device, indicate that the first client cannot check in for the first currently scheduled activity via the first interface device.

27. The system of claim 26 wherein the processor is further programmed to, after determining that the first currently scheduled activity is one of the second subset activities, indicate that the first client must check in for the first currently scheduled activity at the second location.

28. The system of claim 27 wherein the processor is further programmed to identify an estimated travel time for the first client to travel from the first location to the second location and present the estimated travel time to the first client via the first interface device.

29. The system of claim 28 wherein the first activity is scheduled to commence at a first time, the processor further programmed to use the current time and the estimated travel time to identify a predicted arrival time of the first client at the second location and, when the predicted arrival time is subsequent to the first time, provide notice to the first client via the first interface device.

30. The system of claim 29 wherein at least a first resource is required to perform the first activity, the processor further programmed to, when the predicted arrival time is substantially subsequent to the first time, indicate that the first client should reschedule the first activity for a time subsequent to the first time via the first interface device.

31. The system of claim 26 wherein the processor is further programmed to provide instructions via the first interface device directing the first client from the first location to the second location.

32. The system of claim 26 wherein the first and second locations are in different buildings.

33. The system of claim 26 wherein the check in resource at the second location includes a second interface device at the second location for checking clients in for second subset activities and wherein the second interface device can be used to input client identifying information.

34. The system of claim 33 wherein the processor is further programmed to, when client identifying information is provided via the second interface device:
   identify the client as a second client;
   identify at least a first currently scheduled activity for the second client;
   determine that the first currently scheduled activity for the second client is one of the first subset activities; and
   via the second interface device, indicate that the second client must check in for the first currently scheduled activity for the second client via the first interface device.

35. The system of claim 26 wherein the processor is further programmed to perform the steps of:
   identifying at least a second currently scheduled activity for the first client;
   determining that the second currently scheduled activity for the first client is one of the first subset activities; and
   via the first interface device, enabling the first client to check in for the second currently scheduled activity using the first interface device.

* * * * *